United States Patent [19]
Banas et al.

[11] Patent Number: 5,749,880
[45] Date of Patent: May 12, 1998

[54] ENDOLUMINAL ENCAPSULATED STENT AND METHODS OF MANUFACTURE AND ENDOLUMINAL DELIVERY

[75] Inventors: Christopher E. Banas, Mesa; Tarun J. Edwin, Chandler, both of Ariz.

[73] Assignee: Impra, Inc., Tempe, Ariz.

[21] Appl. No.: 508,033

[22] Filed: Jul. 27, 1995

Related U.S. Application Data

[63] Continuation-in-part of Ser. No. 401,871, Mar. 10, 1995.

[51] Int. Cl.$^6$ .................................................. A61M 29/00
[52] U.S. Cl. .................................................. 606/198; 623/12
[58] Field of Search .................................... 606/191–200, 606/151; 623/1, 11, 12

[56] References Cited

U.S. PATENT DOCUMENTS

| | | |
|---|---|---|
| 4,416,028 | 11/1983 | Eriksson et al. . |
| 4,503,569 | 3/1985 | Dotter . |
| 4,512,338 | 4/1985 | Balko et al. . |
| 4,580,568 | 4/1986 | Gianturco . |
| 4,731,073 | 3/1988 | Robinson . |
| 4,739,762 | 4/1988 | Palmaz . |
| 4,816,339 | 3/1989 | Tu et al. . |
| 4,955,899 | 9/1990 | Della Corna . |
| 4,969,896 | 11/1990 | Shors . |
| 5,078,726 | 1/1992 | Kreamer . |
| 5,084,065 | 1/1992 | Weldon et al. . |
| 5,102,417 | 4/1992 | Palmaz . |
| 5,123,917 | 6/1992 | Lee . |
| 5,156,620 | 10/1992 | Pigott . |
| 5,163,951 | 11/1992 | Pinchuk et al. . |
| 5,195,984 | 3/1993 | Schatz . |
| 5,211,658 | 5/1993 | Clouse . |
| 5,282,846 | 2/1994 | Schmitt . |
| 5,282,848 | 2/1994 | Schmitt . |
| 5,282,860 | 2/1994 | Matsuno et al. . |
| 5,334,201 | 8/1994 | Cowan . |
| 5,354,329 | 10/1994 | Whalen . |
| 5,389,106 | 2/1995 | Tower . |

FOREIGN PATENT DOCUMENTS

| | | |
|---|---|---|
| 0 551 179 A1 | 6/1993 | European Pat. Off. . |
| 39 18 736A1 | 12/1990 | Germany . |
| WO 95/05132 | 2/1995 | WIPO . |
| WO 95/05277 | 2/1995 | WIPO . |
| WO 95/05555 | 2/1995 | WIPO . |

*Primary Examiner*—Glenn K. Dawson
*Attorney, Agent, or Firm*—David G. Rosenbaum

[57] ABSTRACT

An radially expandable stent-graft and method of making the same, including at least one a stent member encapsulated between at least two longitudinally expanded polytetrafluoroethylene (ePTFE) coverings. The at least one stent member has openings through wall surfaces of the stent to permit radial expansion. The at least two longitudinally expanded ePTFE coverings are circumferentially applied over the at least one stent member in their unsintered state, and sintered during application of a circumferential pressure to bond the ePTFE around and through the wall surfaces of the stent. The sintered ePTFE forms a substantially continuous, monolithic and integral encapsulation of the at least one stent. Upon radial expansion of the stent-graft, the stent and the ePTFE node-fibril microstructure radially deform. Radial deformation of the ePTFE encapsulation results in nodal elongation in the axis of radial expansion. After radial expansion of the stent-graft, a substantial bonded area remains intact and maintains the encapsulation of the stent in vivo.

21 Claims, 20 Drawing Sheets

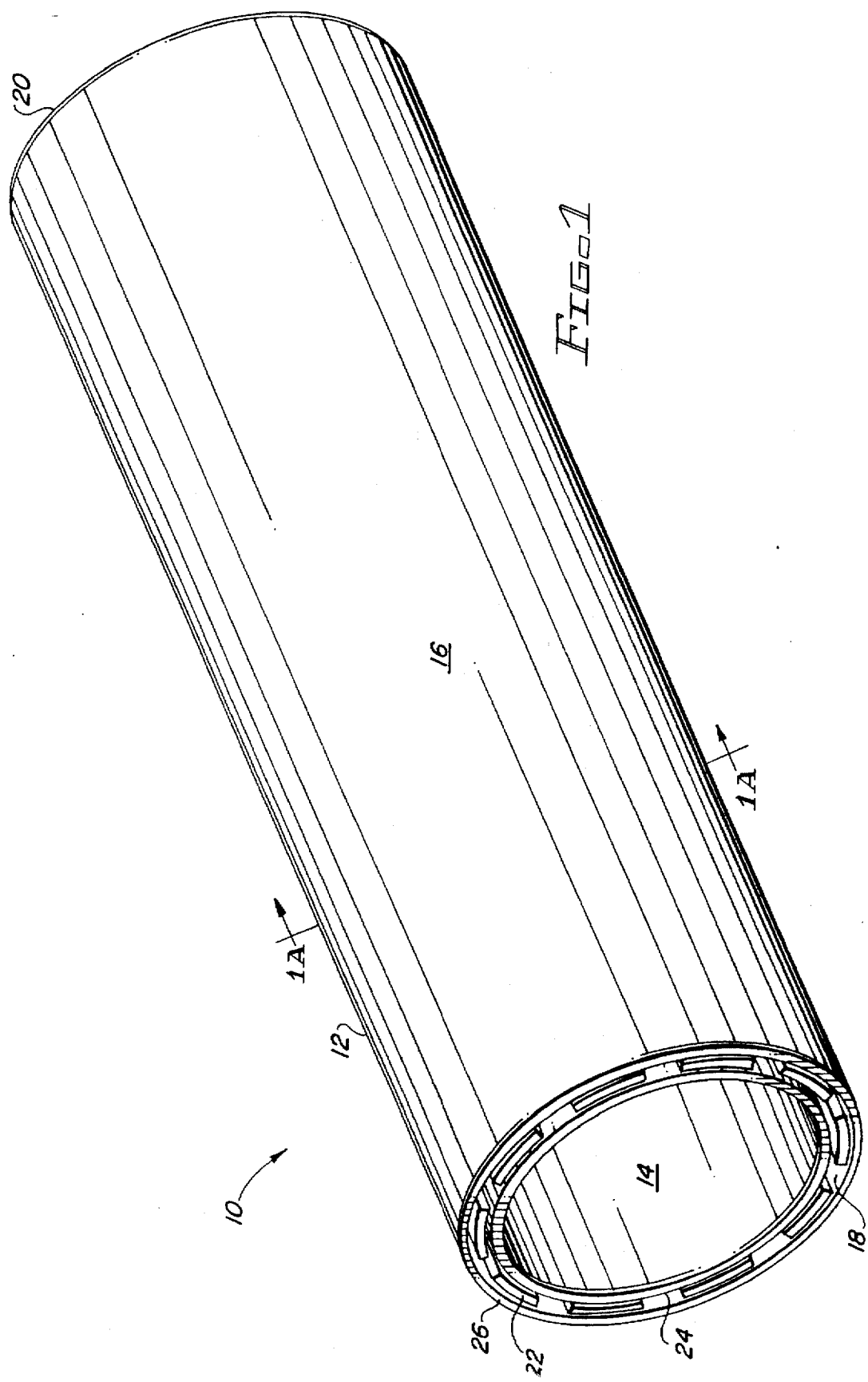

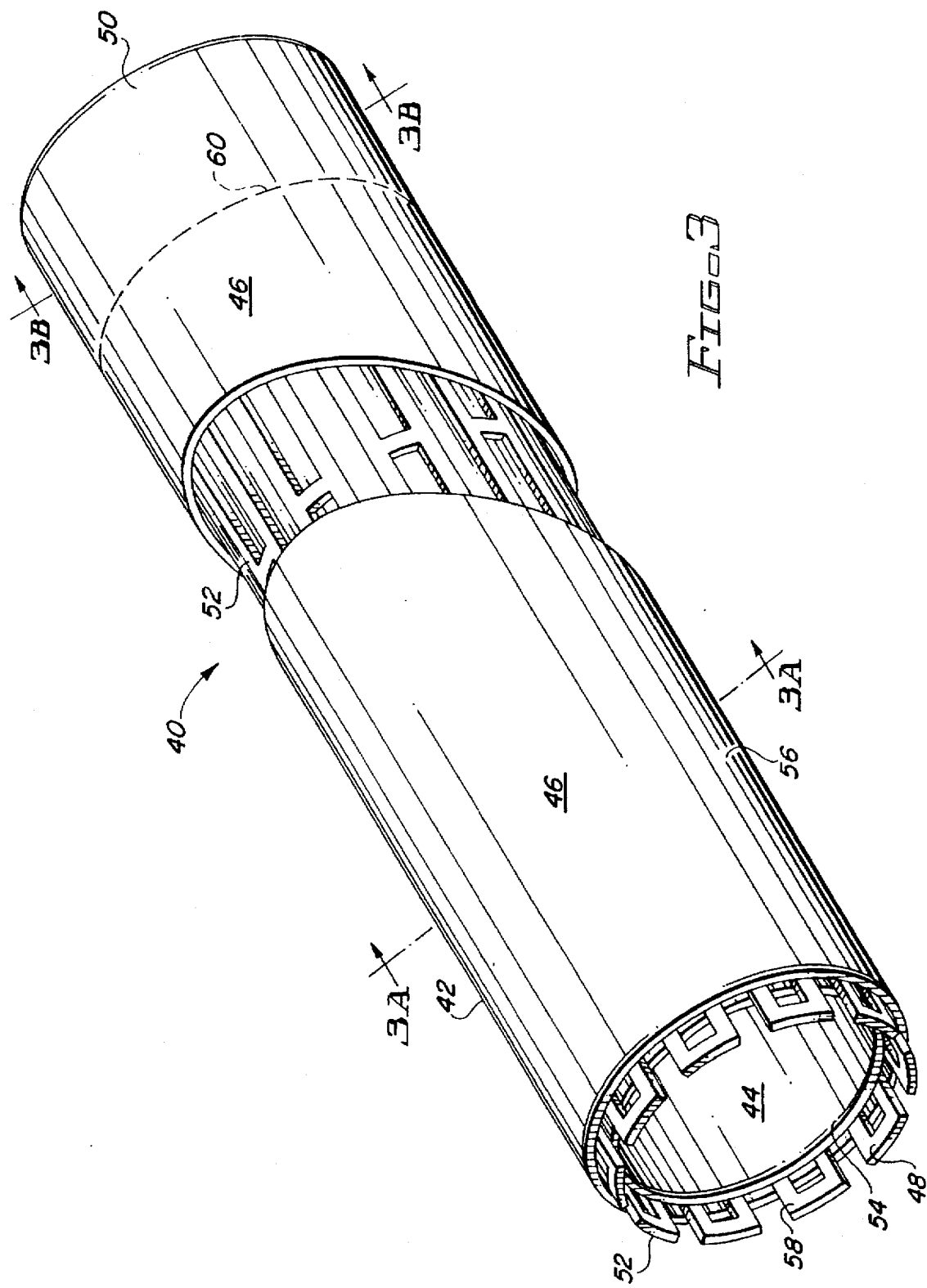

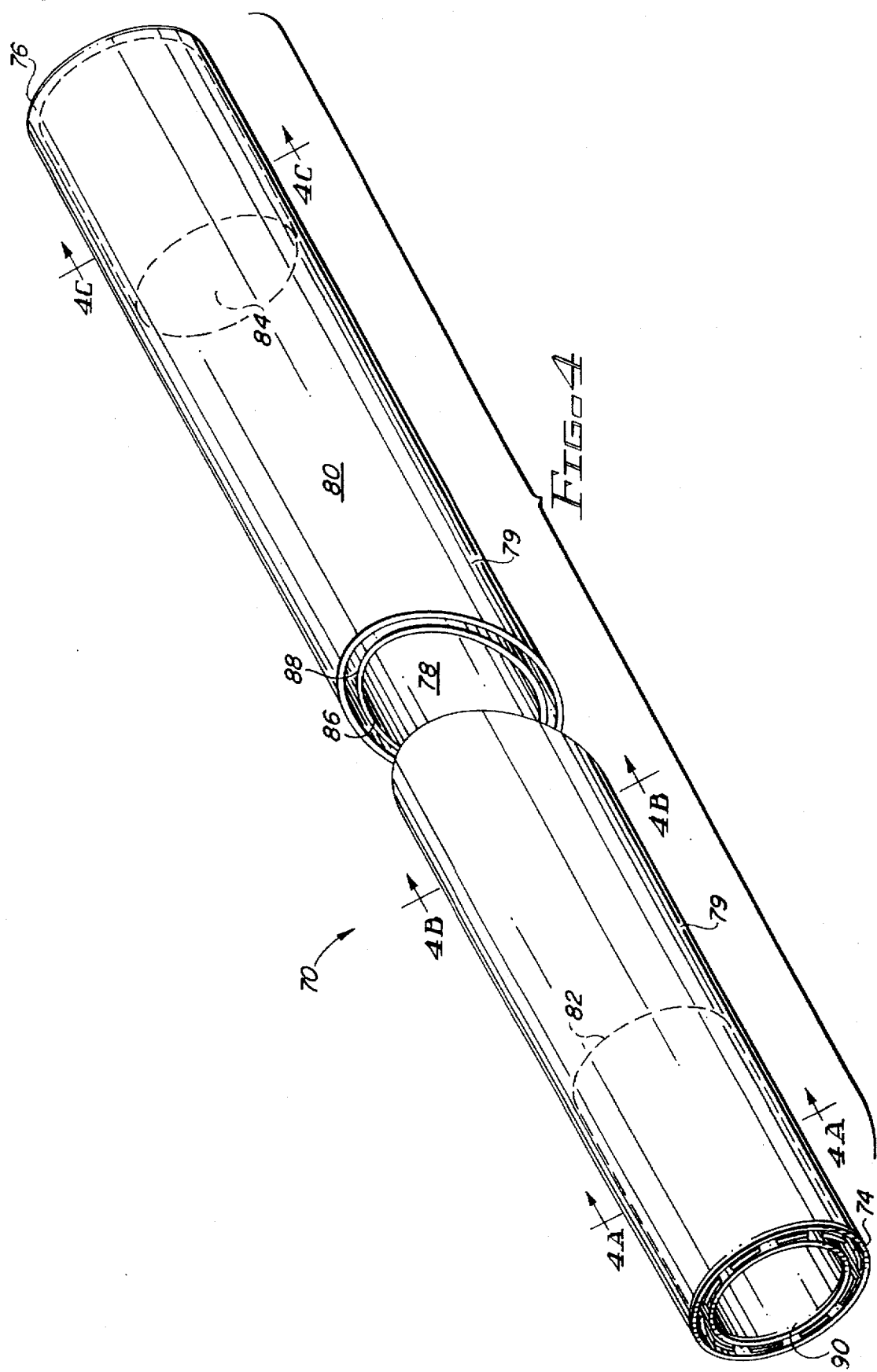

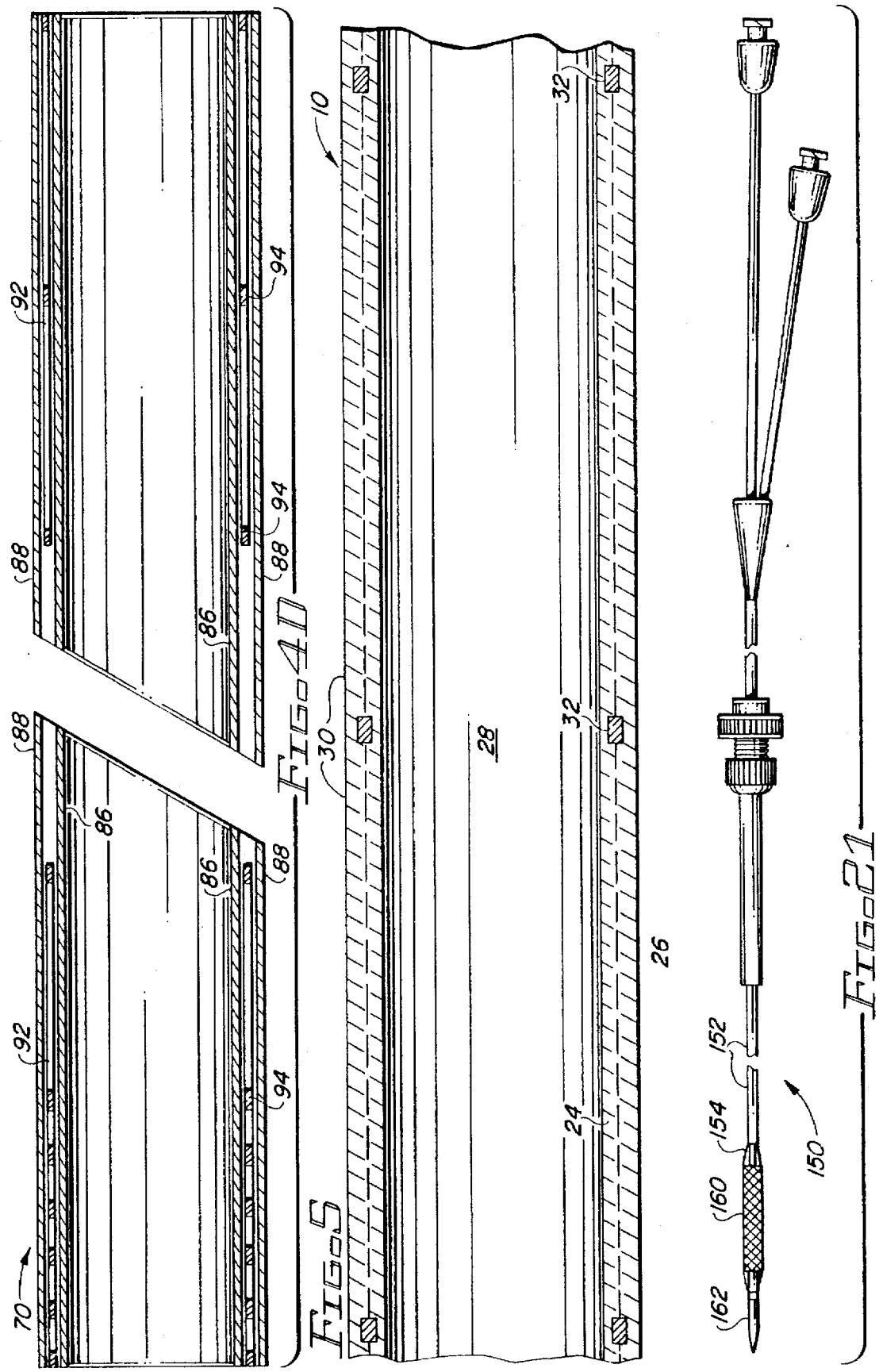

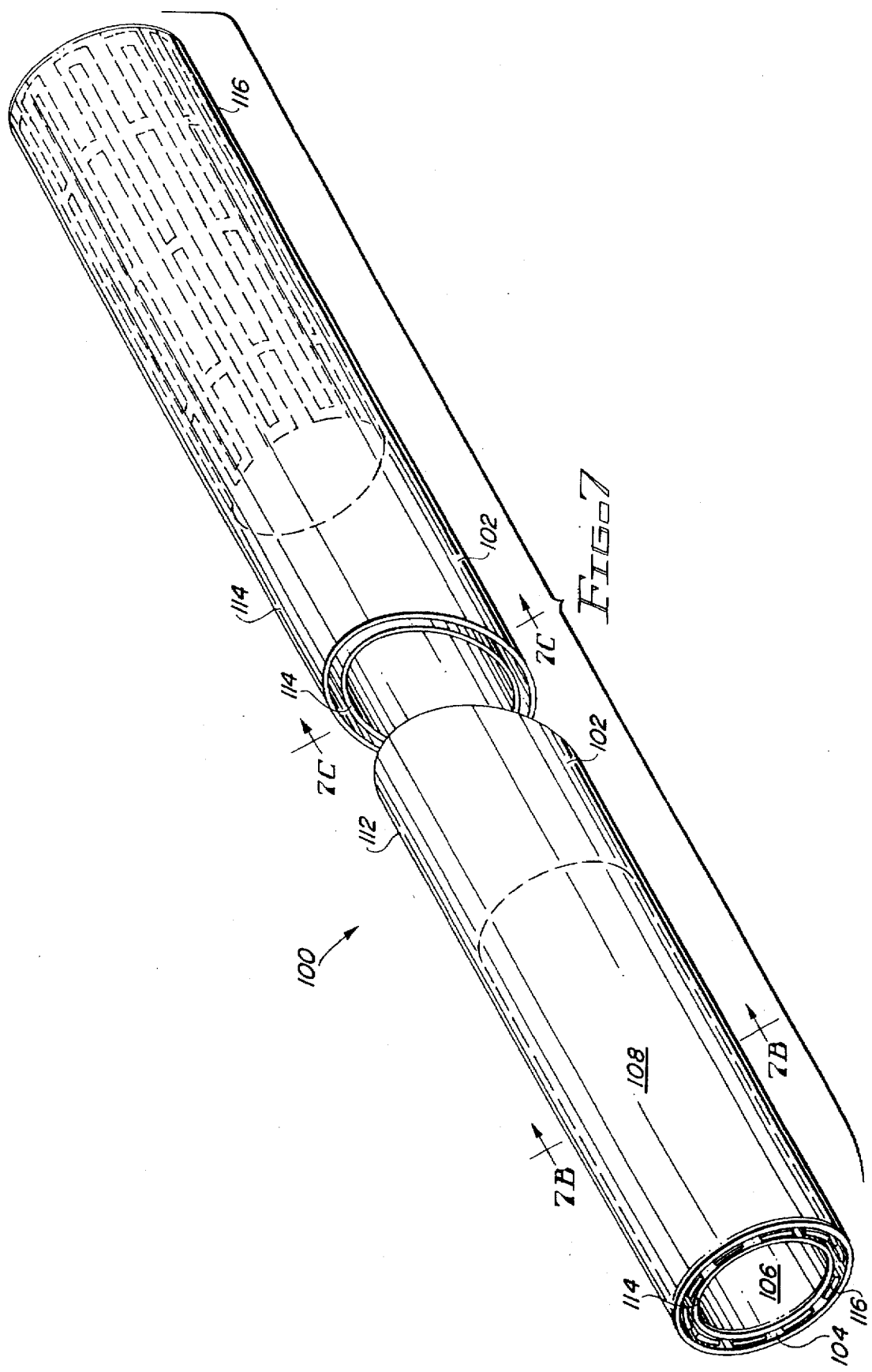

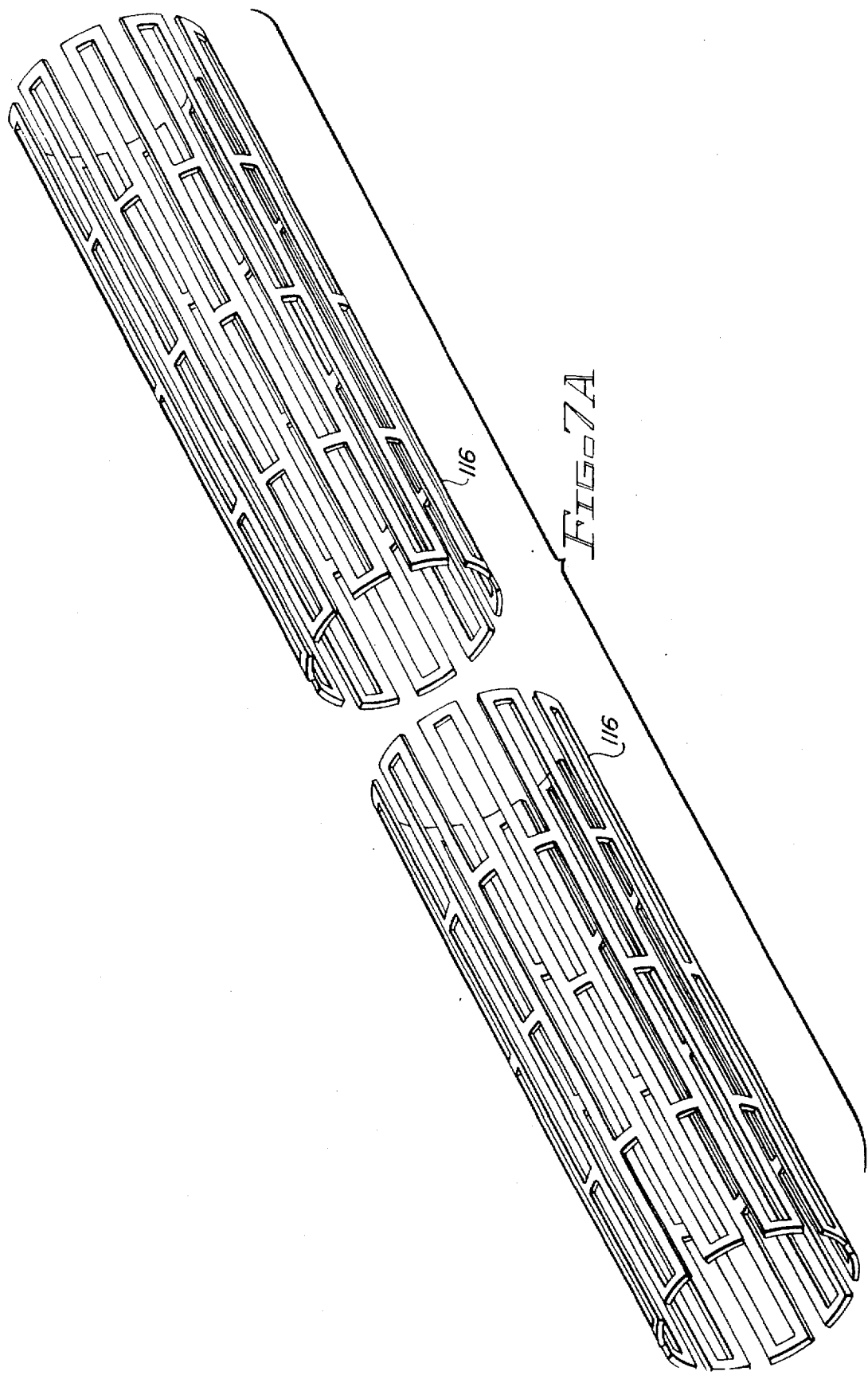

ENDOLUMINAL ENCAPSULATED STENT AND METHODS OF MANUFACTURE AND ENDOLUMINAL DELIVERY

This is a continuation-in-part of copending application Ser. No. 08/401,871 filed on Mar. 10, 1995 pending.

BACKGROUND OF THE INVENTION

The present invention relates generally to an encapsulated endoluminal stent comprising a stent inseparably encased between at least two polytetrafluoroethylene grafts. In accordance with the preferred embodiments of the present invention, the grafts are tubular grafts are longitudinally expanded polytetrafluoroethylene tubular extrudates (ePTFE) and the stent is a pressure-expandable stent. The present invention also provides a method for making the inventive ePTFE encapsulated stent and a method for endoluminal delivery of the inventive ePTFE encapsulated stent. More particularly, a first preferred embodiment of the present invention relates to a radially balloon-expandable encapsulated stent for endovascular delivery which comprises a balloon-expandable tubular stent member interdisposed between two radially balloon-expandable tubular ePTFE grafts. The two radially balloon-expandable tubular ePTFE grafts are made by extruding a PTFE-lubricant mixture through a ram extruder into a tubular shaped extrudate and longitudinally expanding the tubular extrudate to yield a uniaxially oriented node-fibril microstructure in which substantially all of the fibrils in the ePTFE microstructure are oriented parallel to one another in the axis of longitudinal expansion. ePTFE tape or sheet materials may be substituted for the tubular ePTFE grafts.

The method of making the encapsulated stent generally includes the steps of providing a first tubular ePTFE graft member about a mandrel, concentrically positioning a pressure-expandable stent over the first ePTFE graft member such that the first tubular ePTFE graft member covers at least a substantial extent of the luminal surface of the stent, and concentrically positioning a second tubular ePTFE graft member over the stent such that the second tubular ePTFE graft member covers at least a substantial extent of the abluminal surface of the stent, applying an external positive circumferential pressure or an internal radial pressure to assembly to cause a physical interaction and adhesion between the node-fibril microstructure of the first and second ePTFE graft members through wall openings in the stent, and fully sintering the stent-graft assembly to create a substantially monolithic encapsulation of the stent.

BACKGROUND OF THE INVENTION

The use of implantable ePTFE vascular grafts is well known in the art. These types of grafts are typically used to replace or repair damaged or occluded blood vessels within the human body. Vascular grafts, particularly ePTFE vascular grafts are surgically implanted using either end-to-end, side-to-end, or end-to-side anastomoses using sutures to join the graft to a healthy blood vessel. In certain applications, such as in repair of abdominal aortic aneurysm, the grafts are used to exclude the aneurysm by end-to-end anastomosis with healthy aortic tissue proximal and distal to the aneurysm with an unsupported region of the graft subtending and excluding the aneurysm. The graft may be anastomotized using sutures, or use of a radially expanded stent which acts as an attachment between the graft and the healthy aortic tissue.

The use of endoluminal stents, particularly endovascular stents, has been the subject of considerable interest among the medical profession, particularly vascular surgeons. Endovascular stents are presently being used as a post-angioplasty adjunct to maintain the angioplasty-treated blood vessel in an open condition. Examples of endoluminal stents known in the art are pressure-expandable stents which are radially expanded using an angioplasty balloon, as exemplified by the PALMAZ stent described by Julio Palmaz in U.S. Pat. No. 4,733,665, which consists of a tubular perforated metal sleeve, or self-expanding stents which radially expand due to the inherent spring tension of a wire material, as exemplified by the GIANTURCO stent described by Gianturco in U.S. Pat. No. 4,580,568, or Nitinol stents which are radially self-expanding upon application due to exposure to increased temperature, all of which are herein incorporated by reference as examples of stents useful in conjunction with the present invention.

The stent described by Palmaz in U.S. Pat. No. 4,733,665 is used to repair an occluded blood vessel. The Palmaz stent is endovascularly introduced into a blood vessel using a balloon angioplasty catheter, the stent is positioned at the occlusion within the blood vessel, and the balloon is expanded by introducing a fluid under pressure from an external source, through the catheter and into the balloon, thereby expanding the balloon and exerting a radially expansive pressure onto the luminal surface of the stent. The stent is radially expanded from an unexpanded diameter to an expanded diameter which approximates the inner diameter of the blood vessel in its unoccluded state. The balloon catheter is then deflated and removed, while the stent remains seated within the blood vessel due to the radial deformation of the stent against the intimal surface of the blood vessel.

The use of radially expandable stents in combination with a PTFE graft for abdominal aortic aneurysm exclusion is disclosed in U.S. Pat. No. 5,078,726 to Kreamer. Kreamer teaches use of radially balloon-expandable stents, placed within proximal and distal ends of a PTFE graft, to anchor the proximal and distal ends of the PTFE graft to healthy aortic tissue proximal and distal of the aneurysm, with the unsupported section of the PTFE graft spanning the aneurysmal site. The proximal and distal stents are radially expanded by inflating the angioplasty balloon, so that the stents secure the graft ends to the intimal layer of the healthy aortic tissue.

The long-term efficacy of stent placement has been found to increase patient survival, but re-stenosis at the lesion site occurs in approximately 30% of cases. It has been hypothesized that the high re-stenosis rate may be due to turbulent blood flow resulting from fluid flow dynamics at the blood-stent interface or intimal hyperplasia occurring through the stent structure.

However, although stents and stent-graft combinations have been used to provide endovascular prostheses which are capable of maintaining their fit against blood vessel walls, other desirable features are lacking. For instance, features such as increased strength and durability of the prosthesis, as well as an inert, smooth, biocompatible blood flow surface on the luminal surface of the prosthesis and an inert, smooth biocompatible surface on the abluminal surface of the prosthesis which facilitates healing and tissue ingrowth to anchor the prosthesis within the blood vessel, are considered to be advantageous characteristics for an implantable vascular graft which have not, heretofore, been achieved.

Attempts to achieve these advantageous characteristics have been made by producing strengthened and reinforced prostheses composed entirely of biocompatible grafts and graft layers. For example, U.S. Pat. No. 5,048,065, issued to Weldon, et al. discloses a reinforced graft assembly comprising a biologic or biosynthetic graft component having a porous surface and a biologic or biosynthetic reinforcing sleeve which is concentrically fitted over the graft component. The reinforcing sleeve includes an internal layer, an intermediate layer, and an external layer, all of which comprise biocompatible fibers. The sleeve component functions to provide compliant reinforcement to the graft component. Further, U.S. Pat. No. 5,163,951, issued to Pinchuk, et al. describes a composite vascular graft having an inner component, an intermediate component, and an outer component. The inner and outer components are preferably formed of expanded PTFE while the intermediate component is formed of strands of biocompatible synthetic material having a melting point less than the material which comprises the inner and outer components.

Another reinforced vascular prosthesis having enhanced compatibility and compliance is disclosed in U.S. Pat. No. 5,354,329, issued to Whalen. The Whalen patent describes a non-pyrogenic vascular prosthesis comprising a multilaminar tubular member having an interior strata, a unitary medial strata, and an exterior strata. The medial strata forms an exclusionary boundary between the interior and exterior strata. Also, one embodiment of the prosthesis is formed entirely of silicone rubber which comprises different characteristics for the different strata contained within the graft.

The prior art also includes grafts having increased strength and durability which have been reinforced with stent-like members. For example, U.S. Pat. No. 4,731,073, issued to Robinson discloses an arterial graft prosthesis comprising a multi-layer graft having a helical reinforcement embedded within the wall of the graft. U.S. Pat. No. 4,969,896, issued to Shors describes an inner elastomeric biocompatible tube having a plurality of rib members spaced about the exterior surface of the inner tube, and a perforate biocompatible wrap circumferentially disposed about, and attached to, the rib members.

Another example of a graft having reinforcing stent-like members is disclosed in U.S. Pat. No. 5,123,917, issued to Lee. The Lee patent describes an expandable intraluminal vascular graft having an inner cylindrical tube, an outer cylindrical tube concentrically enclosing the inner tube, and a plurality of separate ringlike scaffold members positioned between the inner and outer tubes. Further, U.S. Pat. No. 5,282,860, issued to Matsuno, et al. discloses a multi-layer stent comprising an outer resin tube having at least one flap to provide an anchoring means, an inner fluorine-based resin tube and a mechanical reinforcing layer positioned between the inner and outer tubes.

Another stent containing graft is described in U.S. Pat. No. 5,389,106 issued to Tower. The Tower patent discloses an impermeable expandable intravascular stent which includes a distensible frame and an impermeable deformable membrane interconnecting portions of the frame to form an impermeable exterior wall. The membrane comprises a synthetic non-latex, non-vinyl polymer while the frame is comprised of a fine platinum wire. The membrane is attached to the frame by placing the frame on a mandrel, dipping the frame and the mandrel into a polymer and organic solvent solution, withdrawing the frame and mandrel from the solution, drying the frame and mandrel, and removing the mandrel from the frame.

Although the previously described reinforced grafts disclose structures have increased strength and durability, as well as inert, smooth inner and outer surfaces to reduce thrombogenicity, the prior art references do not disclose a device which exhibits increased strength and durability of the prosthesis, a smooth, biocompatible blood flow surface on the luminal surface of the prosthesis and an inert, smooth biocompatible surface on the abluminal surface of the prosthesis which facilitates tissue ingrowth to anchor the prosthesis within the blood vessel, resistance to radial constriction or collapse, and self-anchoring. Accordingly, there is a need for a radially expandable reinforced vascular graft which has a low profile for endoluminal delivery, is radially expandable in vivo, is resistant to radial constriction and collapse after radial expansion, is biocompatible, provides a smooth luminal blood flow surface, is substantially non-thrombogenic, provides a microporous abluminal surface to encourage tissue ingrowth and endoluminal anchoring of the device, is substantially non-thrombogenic and exhibits increased patency.

SUMMARY OF THE INVENTION

It is a principal object of the present invention to provide a reinforced endoluminal graft in the form of an endoluminal stent encapsulated by tubular ePTFE grafts.

It is another principal object of the present invention to provide an intraluminal stent-graft in which no body tissue or body fluid is exposed to the material of the stent. Particularly, in endovascular applications, it is an object of the present invention to provide a stent-graft having no metal exposed to contact blood.

It is another objective of the present invention to provide an intraluminal encapsulated stent-graft useful for reinforcing and maintaining luminal anatomic passageways in an unoccluded unconstricted, or unweakened state and which is useful in blood vessels for exclusion of aneurysms, vascular shunts and bypasses, and focal and diffuse vascular lesions, or in other anatomical passageways such as biliary ducts, ureters, the urethra, or similar luminal structures.

It is a further object of the present invention to provide an ePTFE encapsulated endoluminal stent in which both the stent and the ePTFE encapsulation surrounding the stent are radially expandable, with the ePTFE encapsulation node-fibril microstructure radially deforming during radial expansion of the stent-graft.

It is a still further objective of the present invention to provide a radially expandable ePTFE encapsulated endoluminal stent which is characterized by a low profile to facilitate percutaneous endoluminal delivery and which is which is characterized by having an inert, smooth, biocompatible interior and exterior surfaces in both the unexpanded and the expanded states of the stent-graft assembly.

It is a still further objective of the present invention to provide a stent-graft assembly having reduced thrombogenicity due to eliminating intravascular metal-blood contact with an ePTFE encapsulation covering the luminal and abluminal surfaces of the stent-graft and each opposing end of the stent-graft.

It is yet another objective of the present invention to provide an ePTFE encapsulated endoluminal stent having an unseamed, smooth luminal surface which presents a substantially non-turbulent blood interface to reduce thrombogenicity associated with blood flow across the luminal surface of the ePTFE encapsulated endoluminal stent.

It is still a further object of the present invention to provide a reinforced vascular graft in the form of an encapsulated stent that is radially expandable in vivo using a conventional balloon catheter and which is readily disengaged from the expansion balloon without radial collapse or constriction of the encapsulated stent, or any portion thereof.

It is yet a further object of the present invention to provide a one-piece radially expandable reinforced vascular graft which comprises a radially expandable stent or similarly structured radially expandable support layer encased between dual ePTFE graft layers which form a monolithic encapsulation of the stent.

It is a still further object of the present invention to provide an encapsulated stent which comprises a stent member concentrically interdisposed between two extruded, tubular PTFE or ePTFE graft members.

It is a still further object of the present invention to provide an encapsulated stent which comprises at least one stent member concentrically interdisposed between at least two tubular ePTFE extrudates, each of the at least two tubular ePTFE extrudates having a substantially uniaxial fibril microstructure oriented parallel to the longitudinal axis of the at least one stent member.

It is yet another object of the present invention to provide a stent-graft assembly which comprises a tubular radially balloon-expandable stent circumferentially positioned between two extruded, expanded and unsintered tubular PTFE grafts, wherein the length of the ePTFE grafts are less than, equal to, or greater than the length of the stent at an expanded diameter of the stent-graft assembly after sintering the ePTFE on the stent-graft assembly and radial expansion of the stent-graft assembly.

It is still another object of the present invention to provide an longitudinally flexible, radially expandable encapsulated stent comprising at least two tubular radially expandable stents, serially aligned in a longitudinally extending array having a common longitudinal axis, with the longitudinal array of stents being circumferentially interdisposed between at least two tubular ePTFE grafts and positioned entirely within a longitudinal extent of the at least two tubular ePTFE grafts.

It is a further object of the present invention to provide a longitudinally flexible, radially expandable encapsulated stent having at least two tubular radially expandable stents, serially aligned in a longitudinally extending array sharing a common longitudinal axis, circumferentially interdisposed between at least two tubular ePTFE grafts, wherein the length of the PTFE grafts is greater than the combined length of the longitudinal array of stents, in their radially unexpanded condition, and at least one longitudinal region of the at least two tubular ePTFE grafts is radially unsupported by the stents, thereby providing articulating regions of the stent-graft assembly.

It is another object of the present invention to provide a method for making an encapsulated stent which comprises concentrically interdisposing a radially expandable stent between luminal and abluminal layers of unsintered ePTFE and sintering the assembly to form a radially expandable stent-graft assembly characterized by having a radially expandable stent component and a radially expandable graft component.

These and other objects, features and advantages of the present invention are met by providing a stent-graft assembly which generally comprises a radially expandable reinforced vascular graft which includes a first layer of biocompatible graft material, a second layer of biocompatible graft material, and a support structure interdisposed between the first and second layers of biocompatible material. The first and second layers of biocompatible graft materials are preferably comprised of PTFE extruded into tubular shapes by ram extruding a PTFE-lubricant mixture through a ram extruder into a tubular shaped extrudate and longitudinally expanding the tubular extrudate to yield a uniaxially oriented node-fibril microstructure in which substantially all of the fibrils in the ePTFE microstructure are oriented parallel to one another in the axis of longitudinal expansion. The support structure preferably comprises a stent which is made from any of a number of strong non-elastic materials which are radially self-expandable, ie., those which radially expand under the influence of inherent spring tension of the material configuration or are pressure expandable under the influence of an externally applied pressure, such as a PALMAZ stent which is radially expandable using an angioplasty balloon. Suitable stents are made from Nitinol, silver, titanium, stainless steel, gold, tantalum, or alloys thereof, or any suitable plastic material capable of maintaining its shape and material properties at sintering temperatures and having the necessary strength and elasticity to enable uniform radial expansion without radial constriction or collapse. Examples of suitable stents are those described in Palmaz, U.S. Pat. No. 4,733,665 or as described by Gianturco in U.S. Pat. No. 4,580,568, both of which are herein incorporated by reference as examples of stents useful in conjunction with the present invention.

A first preferred embodiment of the present invention consists of a radially expandable reinforced vascular graft which comprises a tubular stent cover having a first biocompatible tubular graft member, a support member concentrically positioned about the outer surface of the first biocompatible tubular graft member, and a second biocompatible tubular graft member concentrically positioned about and covering the outer surface of the support member wherein the tubular graft members form inseparable layers without intervening adhesives. The support member preferably comprises a plurality of openings which enlarge during radial expansion of the tubular shaped support member and form open regions which enable the first and second biocompatible members contact one another and bond together through the openings, thereby forming a monolithic structure which encapsulates the tubular member and is incapable of complete separation or delamination from one another or from the support member under the conditions of intraluminal delivery and patency.

It is also preferable, in the first embodiment of the present invention, that the first and second biocompatible tubular graft members are selected to have a longitudinal length which is substantially identical to that of the stent when the stent is in its radially expanded diameter. It is known that radial expansion of stents and grafts results in an axial foreshortening of the stent and graft. Because, in accordance with the preferred embodiment of the invention, the encapsulated stent-graft assembly is radially expanded as a single unit, both the stent and the encapsulating graft material will axially foreshorten, however, not necessarily to the same extent. The extent of axial foreshortening is dependent upon several factors. Among these factors is the structural configuration of the stent, the material of the stent, the unexpanded diameter of the stent, the unexpanded diameters of the first and second graft members, the physical characteristics of the graft members and the material of the graft members. Where a completely covered stent is desired, it has been found advantageous to bond the encapsulating layers of the first and second biocompatible tubular graft members around the opposing ends of the tubular structural support member thereby encasing both the longitudinal aspect and the opposing annular ends of the tubular shaped support member, with a section of the bonded first and second tubular graft members projecting axially from each opposing ends of the stent-graft assembly. The axially projecting section of the bonded first and second tubular graft members provides an additional cover area of the tubular graft members to accommodate a greater axial foreshortening of the graft members relative to the stent during radial expansion of the stent-graft assembly.

In accordance with a second preferred embodiment of the present invention, the first and second biocompatible tubular members are selected to have a longitudinal length which is less than that of the support member in its radially expanded diameter. Where the first and second biocompatible tubular members have a longitudinal length less than that of the support member, the first and second biocompatible members are positioned about an intermediate longitudinal section of the support member and the opposing ends of the support member are uncovered by either the first or second biocompatible tubular member. Upon radial expansion using a balloon catheter, the stent-graft assembly radially expands and the exposed uncovered opposing ends of the support member flare outwardly forming outwardly tapered regions of the support member. The outwardly flared opposing ends of the support member impinge upon and seat into intraluminal tissue, such as the neointimal layer of a blood vessel, and serve to anchor the stent-graft assembly within the luminal tissue and provide generally funnel-shaped fluid flow entry and exit regions of the stent-graft assembly.

According to a third preferred embodiment of the present invention, there is provided a longitudinally flexible articulating stent-graft assembly which comprises a first biocompatible tubular graft member having a longitudinal dimension, a second biocompatible tubular graft member having a longitudinal dimension substantially equal to that of the first biocompatible tubular graft member, and a plurality of support members interdisposed between the first and second biocompatible tubular graft members in an end-to-end longitudinal array with annular spaces between adjacent support members. When the plurality of support members are interdisposed between the first and second biocompatible tubular graft members, an entire longitudinal extent of the inner surface of each of the plurality of support members resides adjacent to and in contact the outer surface of the first biocompatible tubular graft member, while at least substantial longitudinal extent of the outer surface of each of the plurality of support members resides adjacent to and in contact with a portion of the second biocompatible tubular graft member, thereby encasing the stent between the first and second biocompatible tubular graft members. In this manner, the first and second tubular graft members encapsulate each of the plurality of stents or supports and at least one longitudinal region of the first and second biocompatible tubular graft members is unsupported by a support member or stent.

Other types of structural supports may also be encapsulated between inner and outer biocompatible members as described above to form varying embodiments of the reinforced vascular graft. For example, an expandable, an articulated reinforced vascular graft may be formed by forming a structural support assembly comprising multiple stent members co-axially aligned in a linear array with each of the multiple stent members being spaced apart from one another and covering the structural support assembly by interdisposing the structural support assembly between at least two biocompatible tubular graft members. The resulting structure is an expandable, articulated reinforced vascular stent-graft having a monolithic encapsulation surrounding the structural support assembly which is incapable of separation from the structural support assembly or delamination.

The first and second biocompatible tubular members preferably comprise unsintered ePTFE tubular extrudates. The first biocompatible tubular member is preferably selected as the luminal tubular member, is extruded as a tube having an outer diameter less than the inner diameter of the unexpanded support member, or stent, such that the unexpanded stent may be concentrically placed over and circumferentially surround the first biocompatible tubular member with a close tolerance fit. The second biocompatible tubular member is preferably selected as the abluminal tubular member, and is extruded as a tube having an inner diameter greater than the outer diameter of the unexpanded tubular support member, or stent, such that the second biocompatible member may be concentrically placed over and circumferentially surround the unexpanded support member, or stent, with a close tolerance fit. It will be understood by those skilled in the art that unsintered, longitudinally expanded ePTFE tubular extrudates have low radial strength and are prone to fracturing. Dimensional control during the PTFE extrusion process and longitudinal expansion is especially important to ensure that tubular diameters of the first and second biocompatible tubular graft members are maintained within the predetermined desired tolerances relative to the unexpanded inner and outer diameters of the selected stent.

While specific reference is made to using ePTFE as the biocompatible material, alternative materials may be used, including polyamides, polyimides, silicones, fluoroethylpolypropylene (FEP), polypropylfluorinated amines (PFA), or other fluorinated polymers.

The present invention is also directed to a process for making a radially expandable reinforced vascular graft which includes the steps of:

a) positioning a tubular radially pressure-expandable structural support member, having a plurality of wall openings, over a first biocompatible tubular graft material, the tubular graft material having a luminal and abluminal surface;

b) positioning a second layer of biocompatible tubular graft material having a inner and outer surface over the structural support member such that the structural support member is interdisposed between and at least substantially covered by the first and second biocompatible tubular graft materials; and c) affixing the tubular structural support member between the first and second biocompatible tubular graft material such that the first and second biocompatible tubular graft materials contact one another through the plurality of openings in the tubular support material and form a substantially monolithic encapsulation circumferentially surrounding at least a substantial longitudinal aspect of the tubular support material with all of the layers being substantially inseparable from one another under conditions of endovascular delivery, endovascular placement, radial expansion and under in vivo conditions.

The step of affixing the structural support member to the first and second biocompatible graft materials preferably comprises applying a circumferential or radial pressure to the first and second biocompatible graft materials after they are loaded onto a mandrel and heating the resulting assembly to form a mechanical bond between the first and second biocompatible graft materials. Alternatively, the step of affixing the tubular structural support member to the first and second biocompatible graft materials may include the step of applying at least one of an biocompatible adhesive, an aqueous dispersion of polytetrafluoroethylene, polytetrafluoroethylene, fluoroethylpolypropylene (FEP), polyurethane, polyamide, polyimide or silicone between the biocompatible graft layers and the structural support member and, where a biocompatible adhesive or melt thermoplastic is used, heating the resulting assembly at a melt temperature of the adhesive or melt thermoplastic and below the sintering temperature of the biocompatible graft materials, or in the case of a PTFE interlayer, heating the resulting assembly above the sintering temperature of PTFE. It will be understood that the biocompatible adhesive may be applied as an interlayer or directly to either of the first or second biocompatible graft materials or to the structural support member. Still further, the structural support member may be made with an adhesive integral with the material of the structural support, such as an adhesive bonded to the structural support material, or adhesive microspheres dispersion coated onto or bonded to the structural support member and activated by pressure or elevated temperature.

Further, the process for making a preferred embodiment of the radially expandable reinforced vascular graft of the present invention includes the steps of:

a) selecting a diametrically balloon-expandable stent member having unexpanded and expanded inner and outer diameters and openings in the walls of the stent member which permit radial expansion;

b) concentrically mounting onto a mandrel a first longitudinally expanded, unsintered tubular extrudate of polytetrafluoroethylene having an outer diameter less than that of the unexpanded inner diameter of the selected diametrically expandable tubular support structure, such that the ePTFE tubular extrudate does not substantially radially expand upon mounting onto the mandrel;

c) concentrically engaging the selected stent member, in its unexpanded or substantially unexpanded state, over the first unsintered ePTFE tubular extrudate, d) concentrically mounting over the stent member, a second expanded, unsintered tubular extrudate of polytetrafluoroethylene having a inner diameter greater than the outer diameter of the stent member, such that the second ePTFE tubular extrudate is not substantially radially expanded during engagement over the tubular support structure and the stent member is circumferentially covered by both of the first and second ePTFE tubular extrudates over at least a substantial longitudinal extent of the inner and outer surfaces of the stent member; and e) affixing the first and second tubular ePTFE extrudates to the stent member, to cause the first and second tubular ePTFE extrudates to contact and bond to one another through the wall openings of the stent member, thereby forming an integral monolithic encapsulation which circumferentially encloses at least a substantial longitudinal aspect of the tubular support structure and are substantially inseparable from the tubular support structure and from one another under conditions of mounting onto a balloon catheter, endoluminal delivery, radial expansion and residence within a body.

As in the general process for making an expandable reinforced vascular graft, the step of affixing the first and second tubular graft members to the stent preferably comprises applying a circumferential or radial pressure to the first and second tubular graft members and the stent member while the stent-graft assembly is mounted on a mandrel. While still under the influence of the applied circumferential or radial pressure, the stent-graft assembly is heated to the crystalline melt point of ePTFE to sinter the ePTFE tubular members and bond the ePTFE tubular members to one another through the wall openings in stent. Alternatively, the step of fixing the stent to the first and second biocompatible graft materials may include the step of applying at least one of an biocompatible adhesive, an aqueous dispersion of polytetrafluoroethylene, an ePTFE interlayer, fluoroethylpolypropylene (FEP), polyamide, polyimide, polyurethane or silicone as an adhesive layer between the biocompatible graft layers and the stent. Where a biocompatible adhesive or melt thermoplastic is used, heating the resulting assembly at a melt temperature of the adhesive or melt thermoplastic, but below the sintering temperature of the biocompatible graft materials. In the case of an ePTFE interlayer the entire assembly is heated at a temperature above the crystalline melt point of PTFE.

These and other objects, features and advantages of the present invention will become more apparent to those skilled in the art when taken with reference to the following more detailed description of the preferred embodiments of the invention in conjunction with the accompanying drawings.

BRIEF DESCRIPTION OF THE DRAWINGS

FIG. 1 is a perspective view of a first preferred embodiment of the encapsulated stent of the present invention comprising a tubular shaped stent cover configuration in an unexpanded condition.

FIG. 3 is a perspective view of a second preferred embodiment of the tubular shaped stent cover configuration of the present invention wherein the lengths of the grafts are less than the length of the stent with parts shown cut away to expose the underlying layers.

FIG. 4 is a perspective view of a third preferred embodiment of the encapsulated stent of the present invention comprising a tubular shaped stented graft having two stents, shown in phantom, sandwiched between two grafts wherein a region of the overlapping grafts are unsupported by the stents.

FIG. 4D is a longitudinal cross-section of the tubular shaped stented graft shown in FIG. 4 taken along line 4D—4D of FIG. 4.

FIG. 5 is a partial longitudinal cross-sectional view of the tubular shaped stent cover shown in FIG. 1 after fusing the tubular graft members together through the struts of the stent.

FIG. 7 is a perspective view of a fourth preferred embodiment of the encapsulated stent of the present invention comprising an articulated stented graft having a plurality of stents, shown in phantom, sandwiched between two tubular shaped grafts.

FIG. 7A is the support structure contained within the graft shown in FIG. 7 comprising a plurality of stents.

FIG. 21 is a side elevational view of the inventive stent-graft mounted onto a sheath-less balloon catheter for intraluminal delivery.

DETAILED DESCRIPTION OF THE PREFERRED EMBODIMENTS

Figure 1A:
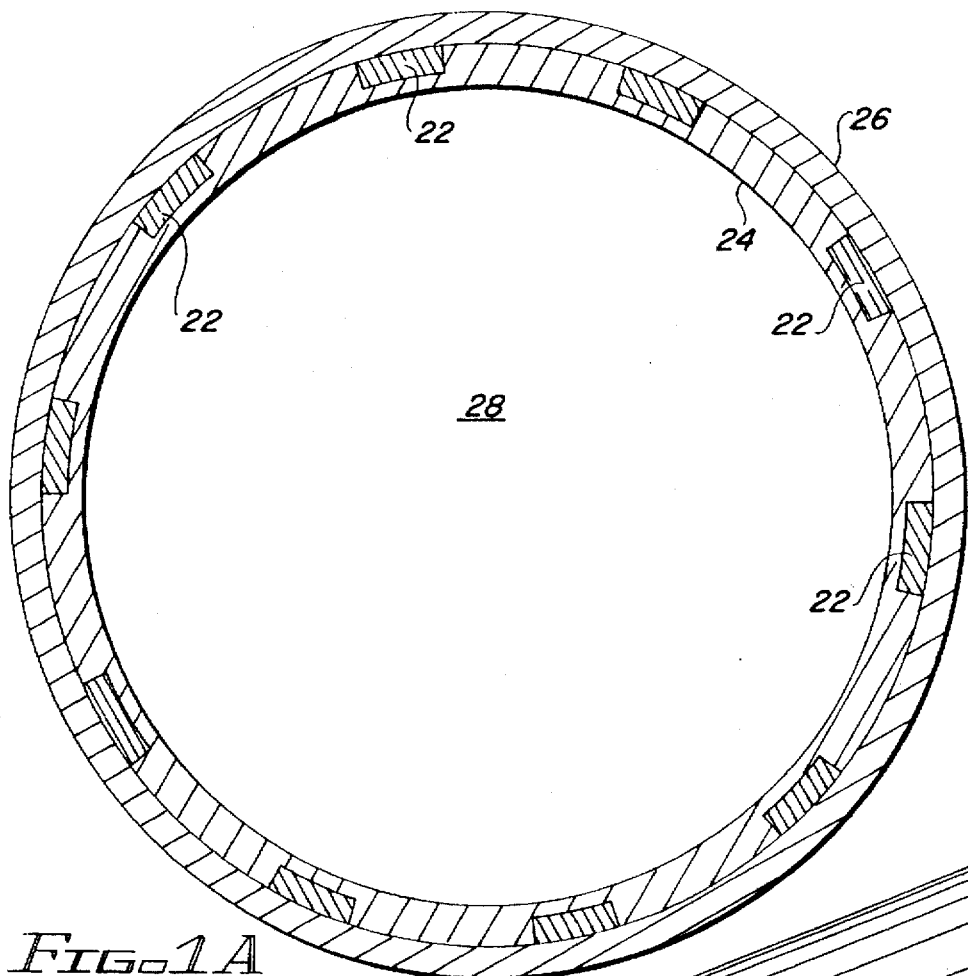
FIG. 1A is a cross-sectional view of the tubular shaped stent cover shown in FIG. 1 taken along line 1A—1A of FIG. 1.

Referring now to the accompanying drawing, in which reference numerals represent various elements of the present invention, a first preferred embodiment of the inventive encapsulated stent 10 is illustrated in FIG. 1. The encapsulated stent-graft 10 generally consists of a tubular member 12 having an interior surface 14 and an exterior surface 16 which are contained between first and second ends 18, 20.

Figure 2:
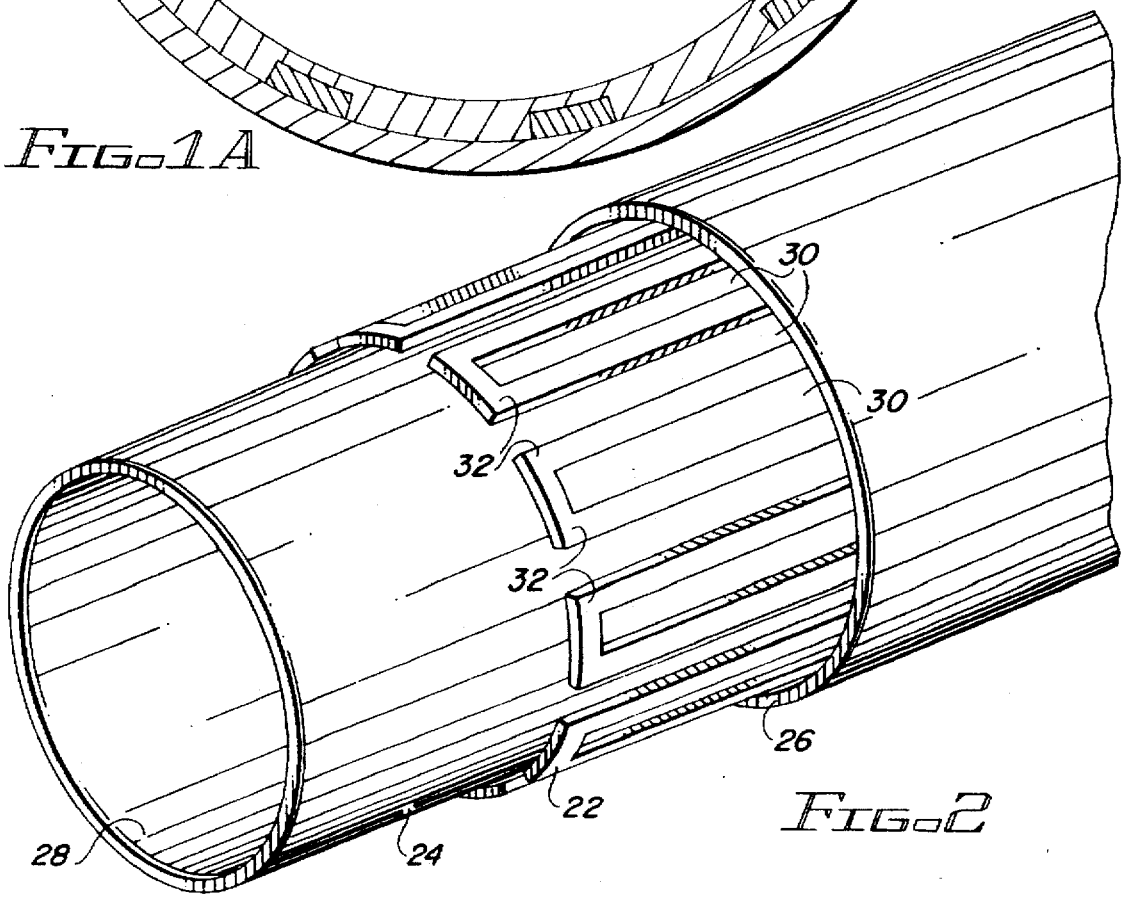
FIG. 2 is a partially exploded view of the first preferred embodiment of the encapsulated stent of the present invention shown in FIG. 1.

As illustrated in FIGS. 1–2, the tubular member 12 comprises a balloon or pressure-expandable tubular support member 22 which is co-axially engaged over a first biocompatible tubular graft member 24 held on a mandrel (not shown). A second biocompatible tubular graft member 26 is then loaded over the first biocompatible tubular graft member/support member combination. The tubular support member 22 preferably comprises a stent like that described in U.S. Pat. No. 4,733,665, issued to Palmaz, and which is herein incorporated by reference, and the first and second biocompatible tubular graft members 24,26 are preferably comprised of expanded polytetrafluoroethylene (ePTFE). The ePTFE first and second biocompatible tubular graft members 24, 26 are made by extruding a PTFE-lubricant mixture through a ram extruder into a tubular shaped extrudate and longitudinally expanding the tubular extrudate to yield a uniaxially oriented fibril microstructure in which substantially all of the fibrils in the ePTFE microstructure are oriented parallel to one another in the axis of longitudinal expansion, as is known in the art and described in U.S. Pat. Nos. 3,953,566, 4,187,390 and 4,482,516 which are expressly incorporated by reference as teaching method of making longitudinally expanded PTFE extrudates.

The first and second biocompatible tubular members 24,26 may, alternatively, be made of unexpanded polytetrafluoroethylene (PTFE), which will be understood by those skilled in the art, to lack the characteristic node-fibril porous microstructure of ePTFE.

The pressure expandable tubular support member 22 is preferably a balloon-expandable PALMAZ-type stent as described more fully in U.S. Pat. Nos. 4,739,726, 4,776,337 and 5,102,417, each of which is incorporated by reference as teaching the type of stent useful with the present invention. Other types of balloon expandable stents useful in the present invention include WIKTOR stents described in U.S. Pat. No. 4,969,458, STRECKER stents described in U.S. Pat. No. 5,405,378, or PALMAZ-SCHATZ stents described in U.S. Pat. No. 5,195,984, all of which are also expressly incorporated by reference as teaching other types of stents useful in the present invention. Alternatively, self expanding stents, such as Nitinol stents or GIANTURCO stents described in U.S. Pat. No. 4,580,568, or WALSTENTs described in U.S. Pat. No. 4,544,771, all incorporated by reference as exemplifying self expanding stents. Where a self-expanding stent is used, however, the inherent spring tension of the stent must exert sufficient radial pressure to radially expand the sintered first and second tubular graft members encapsulating the stent. Regardless of whether a balloon-expandable stent or a self-expandable stent is used, the stent should be made of a material having sufficient strength and deformability to permit radial expansion and resist radial collapse when in the diametrically expanded condition. Examples of materials known in the art are silver, titanium, stainless steel, gold alloys, and any suitable plastic material capable of maintaining its shape and material and mechanical properties at the sintering temperature of PTFE.

A cross sectional view of the tubular stent-graft 10 in its diametrically unexpanded state and prior to fusing the first and second biocompatible members 24, 26. The first biocompatible tubular graft member 24, preferably comprised of unsintered ePTFE, forms the innermost or luminal surface of the tubular stent-graft 10. First biocompatible tubular graft member 24 circumferentially covers at least a substantial longitudinal aspect of the lumen 28 of the tubular support member 22 and forms an inert, smooth fluid flow surface to facilitate non-turbulent fluid flow through the lumen 28. Non-turbulent fluid flow is particular important where the fluid is blood. It will be understood by those in the art that blood flow surfaces which increase flow turbulence have associated increased incidence of thrombus formation.

The tubular support member 22 is preferably a balloon expandable PALMAZ-type stent as more fully disclosed and described in U.S. Pat. No. 4,733,665, which is incorporated by reference as describing a type of radially expandable intravascular stent having a plurality of struts and openings defining the tubular walls of the stent. The tubular support member 22 forms an intermediate layer of the inventive encapsulated stent-graft 10 and circumferentially surrounds an entire longitudinal section of the first biocompatible tubular graft member 24.

The second biocompatible tubular graft member 26, which is also preferably comprised of unsintered ePTFE, constitutes an outermost or abluminal layer of the tubular stent-graft 10.

The use of unsintered of partially sintered ePTFE tubular extrudates as the first and second biocompatible tubular graft members 24, 26 is preferred over fully sintered ePTFE materials, whether in tubular form or in sheet form. While the use of fully sintered ePTFE sheet or tube materials increase ease of manufacture, these materials do not fully bond to one another during subsequent sintering, are incapable of forming a substantially monolithic structure from two separate and discrete ePTFE pieces, have material properties which are adversely affected by additional sintering which is characterized by a corrupted node and fibril microstructure in the ePTFE and the resulting material has compromised expandability. Because it is advantageous, in accordance with the present invention, to provide a stent covering which radially expands concomitantly with the stent, the ePTFE material used to cover the stent has a microstructure which is substantially undisturbed during processing and assembly of the stent graft 10 until the final step of fully sintering the ePTFE to encapsulate the stent.

After loading the first and second tubular graft members 24, 26 onto the tubular support member 22, circumferential or radial pressure is applied to the stent graft assembly 10, either by wrapping the assembly with a helical wrap of an ePTFE or TEFLON tape, or placing the stent-graft assembly in a cylindrical press and exerting a radial pressure to the luminal surface or a circumferential pressure to the abluminal surface of the stent-graft assembly 10. The applied pressure causes the first and second biocompatible tubular graft members 24,26 to contact and mechanically bond to one another through the plurality of openings 30 in the support member 22. Where the support member 22 comprises a PALMAZ-type balloon expandable stent, the first and second ePTFE tubular graft members 24, 26 are bond to one another through the openings between adjacent struts, without the need for intervening adhesives, by mechanical interaction between the node-fibril microstructures of the first and second ePTFE tubular graft members 24 and 26. The stent-graft assembly 10, is then heated to the sintering temperature of PTFE to sinter the first and second ePTFE tubular graft members 24, 26 into a substantially monolithic covering which encapsulates the tubular walls of the intervening stent 22. The resulting stent-graft 10 is a substantially non-radially expanded stent 22 encapsulated within luminal and abluminal ePTFE coverings. Because the luminal and abluminal ePTFE coverings form a substantially monolithic covering through the plurality of the openings 30 in the tubular walls of the stent 22, they are inseparable from one another and from the intervening stent 22. Additionally, the first and second ePTFE graft members 24, 26 are preferably of a sufficient longitudinal length to extend beyond the opposing ends of the tubular stent 22, so that the sections projecting past the opposing ends of the tubular stent 22 may also be sintered together forming a substantially monolithic material which encapsulates the annular opposing ends of the stent 22, thereby encapsulating both the tubular walls of the tubular stent 22 and the wall thicknesses of the tubular stent 22 at opposing ends thereof.

Figure 6:
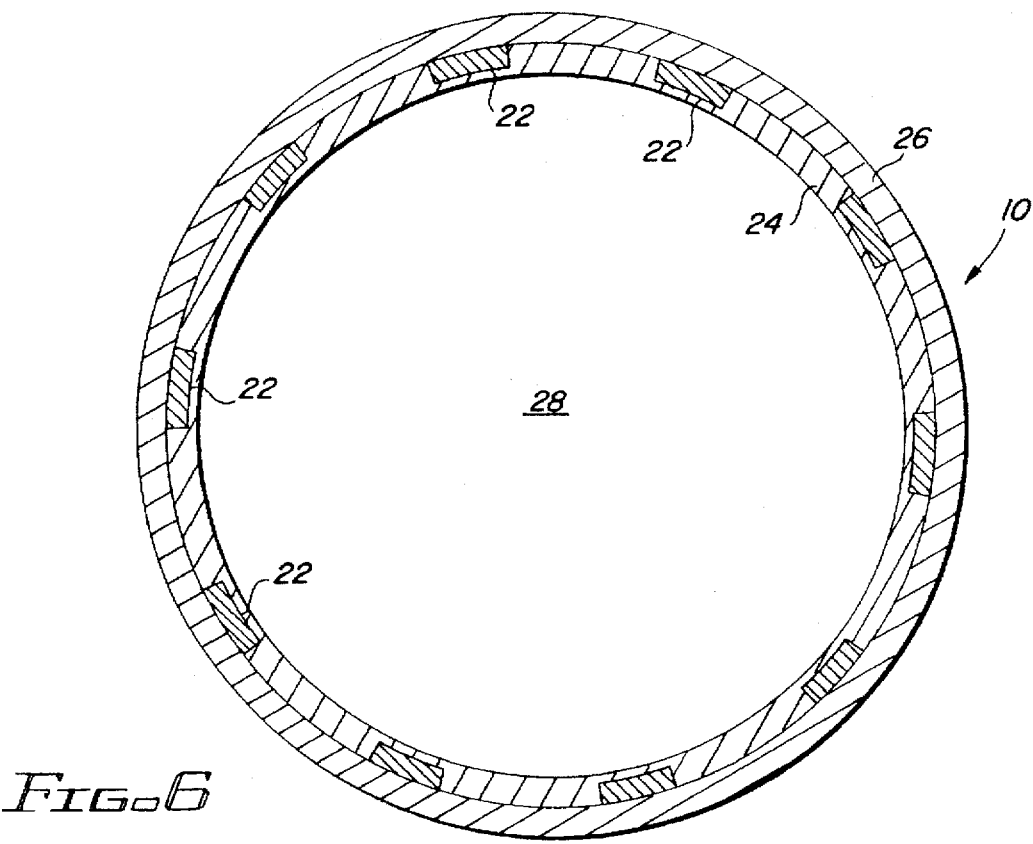
FIG. 6 is a vertical cross-sectional view of the tubular shaped stent cover shown in FIG. 1 after fusing the tubular graft members together through the struts of the stent.

FIG. 5 depicts a partial longitudinal cross-sectional view of the tubular stent graft 10 shown in FIG. 1, but after mechanical bonding and sintering of the first and second ePTFE graft members 24, 26 together through the plurality of openings 30 between adjacent struts of the stent 22. The first and second biocompatible tubular graft members 24, 26 are bonded together through the plurality of openings 30 and form sealed areas 34 between adjacent struts 32 of the support member 22. FIG. 6 depicts a transverse cross-sectional view of the tubular stent graft 10 shown in FIG. 1, but after mechanical bonding of the first and second tubular graft members 24, 26 through the plurality of openings 30 between adjacent struts 32 of the stent 22. As seen in FIG. 6, the first biocompatible tubular graft member 24 forms the inner or luminal layer circumferentially covers the stent lumen 28, thereby forming the luminal fluid flow surface of the tubular stent graft 10. The second biocompatible tubular graft member 26 defines an outermost or abluminal surface of the tubular stent graft 10 and, when endoluminally implanted, resides adjacent and contacts the endoluminal tissue, such as the neointima. The tubular support structure 22, or stent, then forms the intermediate layer of the stent 22 and is circumferentially covered along at least a substantial longitudinal aspect of the stent 22 by the luminal and abluminal tubular graft member coverings 24, 26. It will be understood by those skilled in the art that FIGS. 5 and 6 are exaggerated views of the open areas between the struts 32 of the stent 22. Upon radial expansion of the tubular stent graft 10, the plurality of openings 30 between adjacent struts 32 enlarge in area due to radial deformation of the stent material. However, because the bonded ePTFE material of the first and second biocompatible tubular graft members 24, 26 is also radially expanded, a substantial area of the graft members 24, 26 bonded through the plurality of openings remains bonded after radial expansion of the stent-graft 10.

Those skilled in the art will further understand that the position of the first and second tubular graft members relative to the stent member is interchangeable. That is, the first tubular graft member may be positioned as either a luminal or abluminal position relative to the body passageway or the stent member. Similarly, the second tubular graft member may be positioned as either a luminal or abluminal position relative to the body passageway or the stent member.

Subsequent to applying an external circumferential pressure to the stent graft assembly 10, and fully sintering the stent graft assembly 10 mechanically bond the ePTFE through the pluralist of openings 30 between adjacent struts 32 of the stent 22, the assembly is allowed to cool, removed from the mandrel, trimmed, sterilized and is then ready for endoluminal delivery using a balloon angioplasty catheter.

Turning now back to FIG. 3, a second embodiment of the present invention is illustrated. According to this second preferred embodiment of the invention, there a self anchoring stent-graft 40 is provided. The self anchoring stent-graft 40 employs a covering having a longitudinal length less than that of the stent encapsulated by the covering. In FIG. 3 the self anchoring stent-graft 40 is illustrated in partial cut away to illustrate the underlying elements of the self anchoring stent-graft 40. The self anchoring stent-graft 40 has a luminal surface 44, an abluminal surface 46, and first and second ends 48, 50. The stent-graft 40 includes a pressure expandable stent member 52, preferably of a balloon expandable PALMAZ-type stent as previously described, interdisposed between first and second biocompatible tubular graft members 54, 56, which are preferably comprised of ePTFE. In accordance with this self anchoring stent-graft 40, the stent member 52 is greater in length than each of the first and second biocompatible tubular graft members 54, 56, is uncovered and projects outwardly along the longitudinal axis of the stent-graft 40. The self-anchoring stent-graft 40 is processed as described above in connection with the first preferred embodiment of the stent-graft 10. That is, a circumferential pressure is applied to the stent-graft assembly 40 and the entire assembly 40 is heated to the sintering temperature of ePTFE to fully sinter the first and second biocompatible tubular graft members 54, 56 to one another through the plurality of openings in the stent member 52, thereby forming a monolithic covering on the luminal and abluminal surfaces of the stent-graft assembly 40. The entire stent-graft assembly 40 is then radially expandable from its first unexpanded diameter to a second radially expanded diameter. Upon radial expansion, both the stent member 52 and the monolithic covering made from the first and second biocompatible tubular members 54, 56 radially expand, with the node-fibril microstructure of the ePTFE covering deforming during radial expansion of the ePTFE. The uncovered opposing longitudinal ends 58, 60 of the stent member 52, form radially projecting barbs upon balloon expansion of the tubular stent-graft 40. The radially projecting barbs extend outwardly from the longitudinal axis of the stent-graft and aid in anchoring the stent-graft 40 to the to the targeted blood vessel wall.

It has been found that when using conventional angioplasty balloons to radially expand the stent-graft 40, the stent-graft 40 covers only a portion of the longitudinal aspect of the angioplasty balloon. The proximal and distal ends of the angioplasty balloon are typically not covered by the stent-graft 40. These uncovered sections of the angioplasty balloon, having little resistance to radial inflation, radially inflate before the medial stent-graft covered section of the angioplasty balloon. The resulting torroidal or "dog-bone" shape of the inflated angioplasty balloon radially expands the proximal and distal uncovered ends 58, 60 of the tubular stent-graft 40 to a greater extend than the medial stent-graft covered section of the stent-graft 40. As a result of this torroidal balloon inflation, the ends of the tubular stent-graft 40 form funnel-shaped ends having larger diameters in the proximal and distal aspects of the stent-graft 40 than in the more medial regions of the stent-graft 40. These funnel-shaped ends function to channel the blood flow into and through the stent and act as an internal guide to facilitate subsequent catheterization of the stented vessel, minimize thrombus formation, and facilitate self-anchoring of the stent-graft within the anatomic passageway or blood vessel.

Figure 3A:
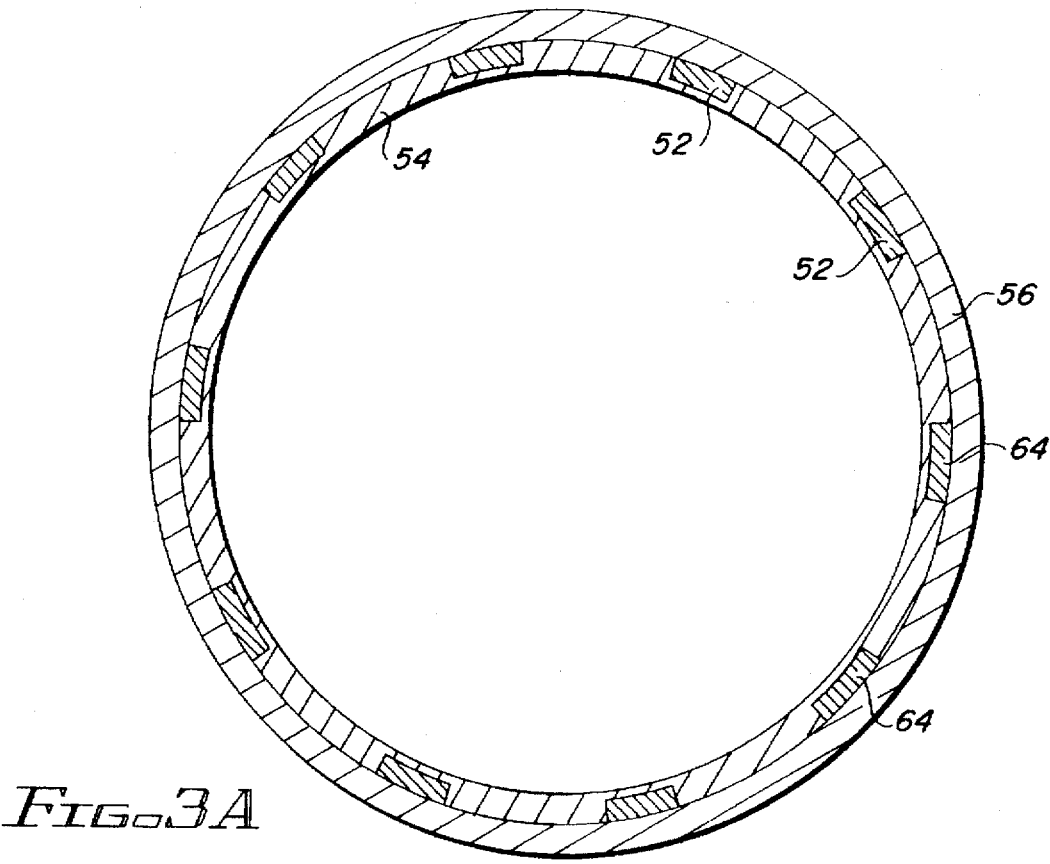
FIG. 3A is a cross-sectional view of the tubular shaped stent cover shown in FIG. 3 taken along line 3A—3A of FIG. 3.

A cross-sectional view taken along line 3A—3A near the center of the alternative tubular stent cover 40 of the present invention illustrated in FIG. 3 is shown in FIG. 3A. The first biocompatible tubular graft member 54 is preferably made of unsintered or partially sintered ePTFE. First biocompatible tubular graft member 54 is positioned on as the innermost luminal layer of the stent-graft 40. The support member or stent 52, preferably comprising a pressure expandable PALMAZ-type, as previously described, circumferentially surrounds the first biocompatible tubular graft member 54 and has a longitudinal length greater than that of the first biocompatible tubular graft member 54. The second biocompatible tubular graft member 56, which also preferably comprises unsintered or partially sintered ePTFE, forms the outermost layer and abluminal surface of the tubular stent-graft 40 and circumferentially covers the stent 52 and has a longitudinal length less than that of the stent 52, but may be greater than, equal to or less than the length of the first biocompatible tubular graft member 54.

Figure 3B:
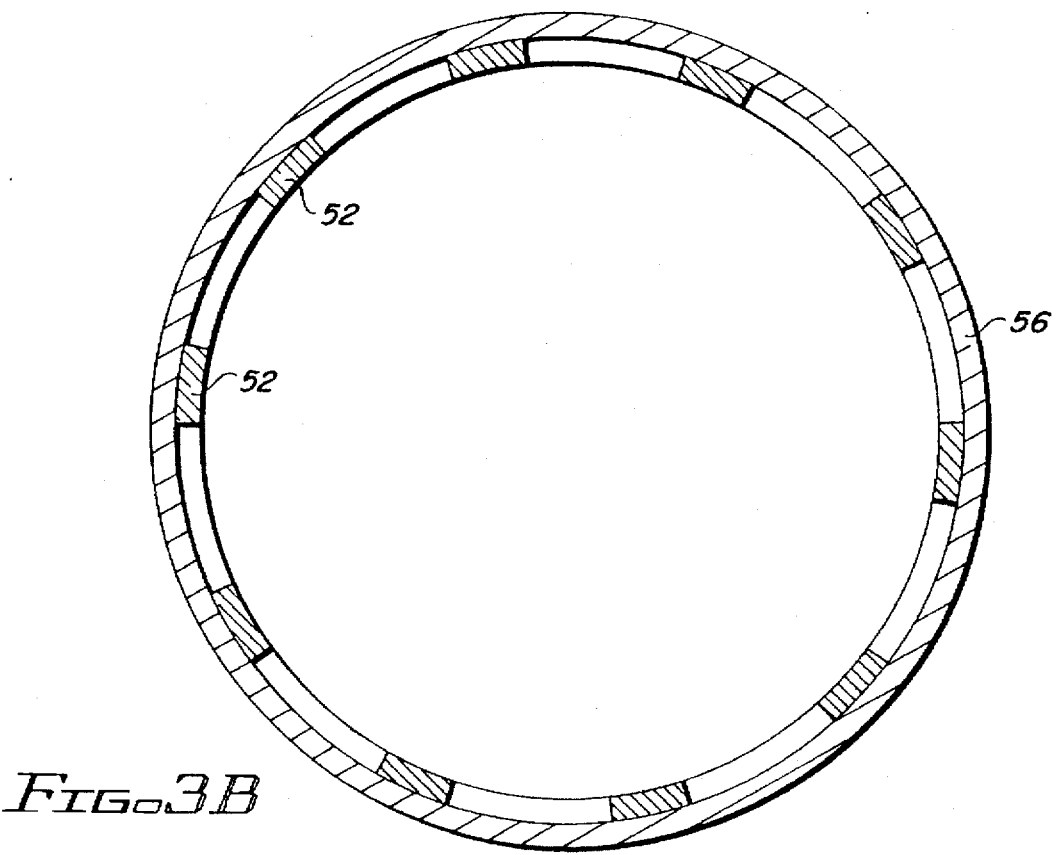
FIG. 3B is a cross-sectional view of the tubular shaped stent cover shown in FIG. 3 taken along line 3B—3B of FIG. 3.

FIG. 3B illustrates a cross-sectional view of the tubular stent-graft 40 taken along line 3B—3B of FIG. 3. It will be seen that the abluminal graft member 54 has a longitudinal length greather than that of the luminal graft member 56. This configuration permits an overhang of the abluminal graft member 54 which facilitates endoluminal placement of a second stent-graft in series with a first stent-graft. After endoluminal delivery and radial expansion of a first stent-graft, a second stent-graft is delivered and positioned in series adjacent the first stent graft. The second stent-graft is concentrically in it unexpanded state concentrically within the overhang region of the abluminal graft member 56 and radially expanded. Upon radial expansion, the overhang region of the abluminal graft member 54, is engaged by one end of the second stent=graft and forms an abluminal covering joining the first and second stent-grafts in series.

Those skilled in the art will further understand that the position of the first and second tubular graft members relative to the stent member is interchangeable. That is, the first tubular graft member may be positioned as either a luminal or abluminal position relative to the body passageway or the stent member. Similarly, the second tubular graft member may be positioned as either a luminal or abluminal position relative to the body passageway or the stent member.

Figure 4A:
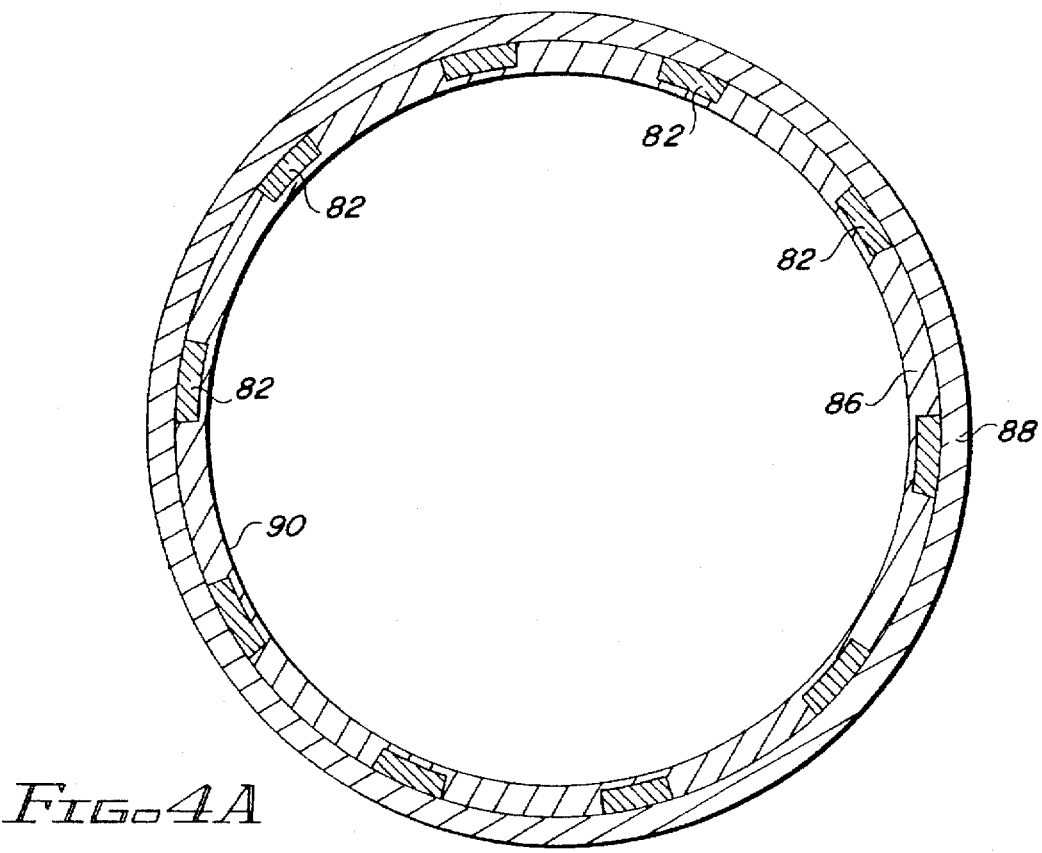
FIG. 4A is a cross-sectional view of the tubular shaped stented graft shown in FIG. 4 taken along line 4A—4A of FIG. 4.
Figure 4B:
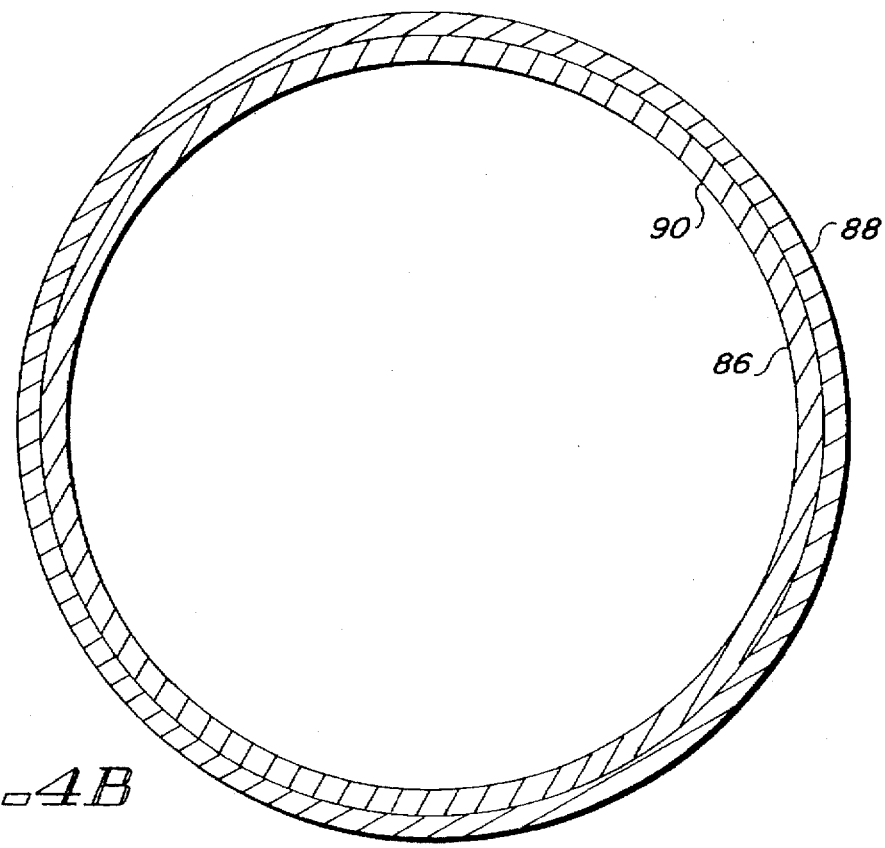
FIG. 4B is a cross-sectional view of the tubular shaped stented graft shown in FIG. 4 taken along line 4B—4B of FIG. 4.
Figure 4C:
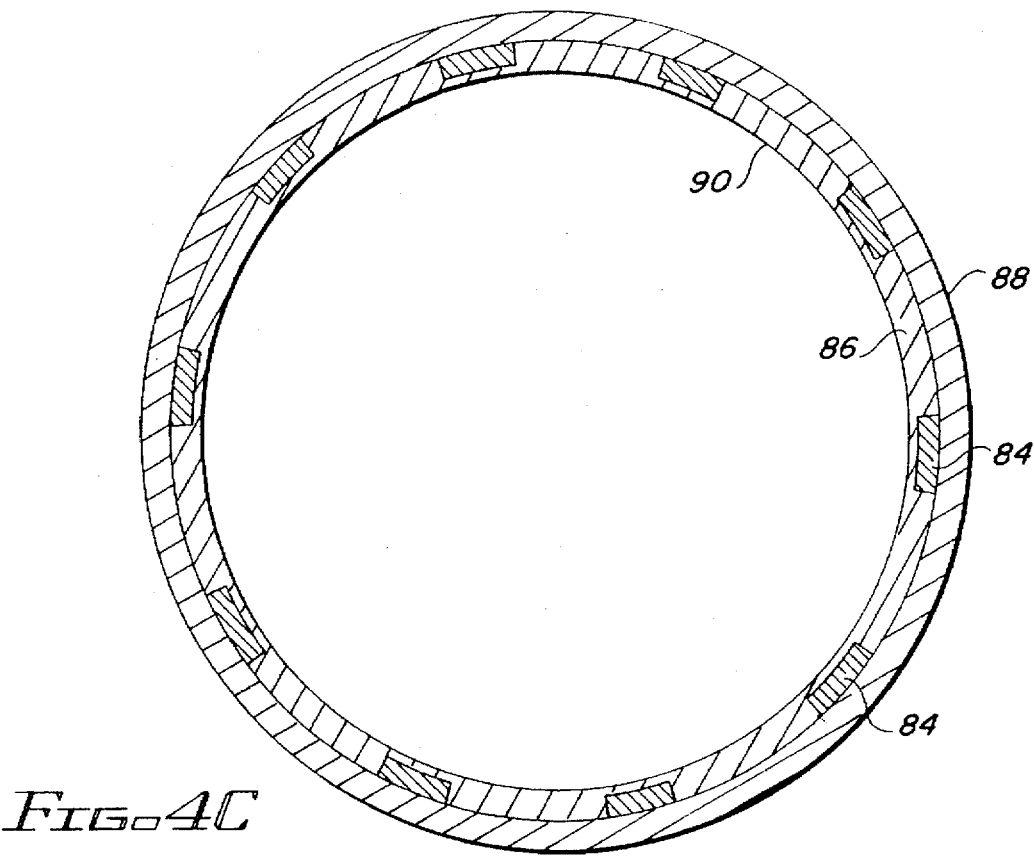
FIG. 4C is a cross-sectional view of the tubular shaped stented graft shown in FIG. 4 taken along line 4C—4C of FIG. 4.

A third preferred embodiment of the encapsulated stent of the present invention is illustrated in FIG. 4 and FIGS. 4A–4D. As shown in FIG. 4, the third preferred embodiment comprises a tubular stent-graft 70 having at least one stent member 82, 84 positioned at each opposing end 74, 76 of the stent-graft 70 and an intermediate longitudinal region of the stent-graft 70 being unsupported by any stent members. The stent-graft 70 has a first end 74, a second end 76, an interior surface 78, and an exterior surface 80. The stent-graft 72 includes first and second radially pressure expandable support members or stents 82, 84, preferably comprising balloon expandable PALMAZ-type stents, as previously described above, shown in phantom. The stent member 82, 84 are concentrically disposed between first and second biocompatible tubular graft members 86, 88, and positioned at opposing ends 74, 76 of the first and second biocompatible tubular graft members 86, 88. An intermediate longitudinal region 79 of the first and second biocompatible tubular graft members 86, 88 is unsupported by the stent members 82, 84. The first and second support or members 82, 84 may, alternatively, comprise structural configurations similar in function to stents, but having different structural configurations which permit radial expansion, resist radial recoil, constriction or collapse, and are made of biocompatible materials. As with the first preferred embodiment of the stent-graft 10, the first and second biocompatible tubular graft members 86,88 are preferably comprised of unsintered or partially sintered ePTFE tubular extrudates. Those skilled in the art will further understand that the position of the first and second tubular graft members 86, 88 relative to the stent member or members 82, 86 is interchangeable. That is, the first tubular graft member 86 may be positioned as either a luminal or abluminal position relative to the body passageway or the stent member. Similarly, the second tubular graft member 88 may be positioned as either a luminal or abluminal position relative to the body passageway or the stent member.

FIGS. 4A and 4C are transverse cross-sectional views are taken along line 4A—4A and line 4C—4C of FIG. 4, respectively, and illustrate end portions of the tubular stent-graft 70. At each of the end portions of the tubular stent-graft 70, a luminal covering is provided by the first biocompatible tubular graft member 86 which forms a luminal fluid flow surface 90 of the stent-graft 70. An abluminal covering is provided by the second biocompatible tubular graft member 88, which provides a tissue contact and ingrowth surface 80 of the stent-graft 70. FIGS. 4A–4D represent the stent-graft 70 prior to bonding and sintering the first and second graft members 86, 88. The first and second tubular support members or stents 82, 84 are concentrically positioned between the first and second tubular graft members 86, 88 and are longitudinally positioned at the first and second ends 76, 78 of the stent-graft 70.

FIG. 4B is a transverse cross-sectional view taken medial the longitudinal length of the stent graft 70 along line 4B—4B of FIG. 4. The unsupported intermediate longitudinal section 79 of the stent-graft 70 consists only of the bonded and sintered first and second biocompatible tubular graft members 86, 88 and is unsupported by any stent member or stent-like structure, but provides an open lumen 90 communicating between the first and second ends 76, 78 of the stent-graft 70.

As with the other embodiments of the present invention described above, the stent-graft assembly 70 is assembled using a madrel to mount the first graft member 86, concentrically mount the first and second stent members 82 and 84 circumferentially around the first graft member 86 and at first and second ends 76, 78, thereof, and circumferentially cover both stent members 82, 84 and the first graft member 88. Both the first and second biocompatible tubular graft members 86, 88 are preferably made of unsintered or partially sintered ePTFE tubular extrudates, are mechanically bonded to one another circumferentially about and longitudinally along the entire stent-graft 70 and through a plurality of openings in each of the stent members 82, 84, and the entire assembly is heated to the sintering temperature of ePTFE to sinter the first and second biocompatible tubular graft members 86, 88 into a substantially monolithic covering encapsulating both stent members 82, 84.

FIG. 4D is a fragmentary longitudinal cross-sectional view taken along line 4D—4D of FIG. 4. Like FIGS. 4A–4C, FIG. 4D represents the stent-graft assembly 70 before mechanical bonding and sintering of the first and second biocompatible tubular graft members 86,88 together through the openings 92 between struts 94 of the first and second support members 82, 84.

The third preferred embodiment of the stent-graft 70 is particularly useful in abdominal aortic aneurysm exclusion procedures where the first and second stent members 82 and 84 are placed proximal and distal the aneurysm, and the intermediate unsupported region 79 of the stent graft 70 excludes the aneurysmal site.

Figure 7B:
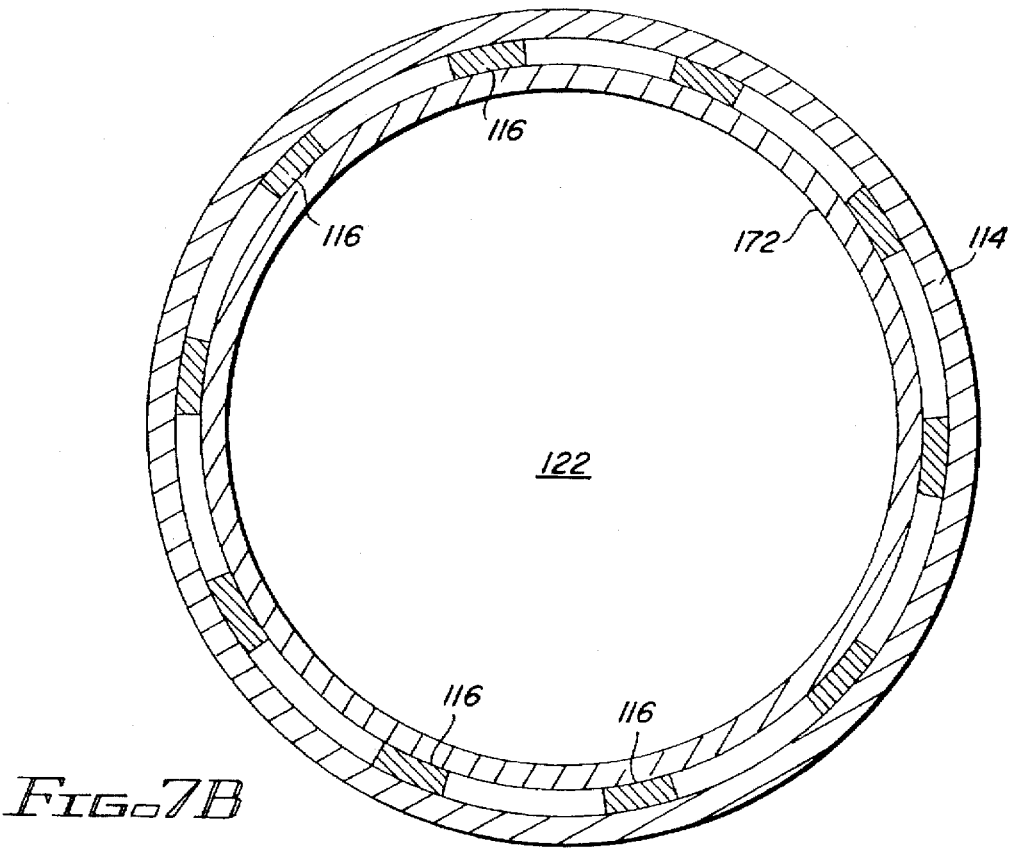
FIG. 7B is a cross-sectional view of the articulated stented graft shown in FIG. 7 taken along line 7B—7B of FIG. 7.

A fourth embodiment of the inventive encapsulated stent-graft 100 is illustrated in FIGS. 7 and 7A–7B. This fourth embodiment of the encapsulated stent-graft 100 is an articulating encapsulated stent-graft in which a plurality of support or stent members 116, co-axially aligned in a longitudinal array in which each of the plurality of stent members 116 are positioned in end-to-end fashion with a small annular space between adjacent ends, are all encapsulated between at least two tubular graft members 112, 114. Articulating stent-graft 100 generally has a first end 104, a second end (not shown), an interior surface 106, and an exterior surface 108. The articulating stent-graft 100 encapsulates a plurality of stent members 116 between first and second tubular biocompatible ePTFE grafts 112, 114. A perspective view of the plurality of stent members is shown in FIG. 7A. The plurality of stent members 116 are spaced apart from one another at a predetermined distance. The spaced apart stent members 116 allow the encapsulated stent 100 to articulate between stent members 116 using the inherent flexibility of an unsupported intervening region 102 of the first and second graft members 112, 114, resident between adjacent stent members 116, as the flexion point. In accordance with an alternate of the articulated encapsulated stent 100, an inter-stent reinforcement member, such as in the PALMAZ-SCHATZ stent referenced above and incorporated hereby reference, may be employed to provide resistance to axial compression and longitudinal foreshortening of the articulated encapsulated stent 100 during radial expansion. Still alternatively, a longitudinally-oriented reinforcing member may be incorporated in or associated with one or more of the ePTFE graft members 112, 114 to provide axial stability to the articulated encapsulated stent 100 and provide resistance to longitudinal foreshortening of the ePTFE graft members 112, 114 and maintain spacing between adjacent stent members 116, while still permitting articulation of the encapsulated stent 100, as more fully described in co-pending and co-owned U.S. patent application Ser. No. 08/439,853 filed May 12, 1995, which is hereby incorporated by reference and priority claimed therefrom.

FIG. 7B is a transverse cross-sectional view taken along line 7B—7B of FIG. 7, near an end of the articulating encapsulated stent-graft 100. The first tubular shaped biocompatible graft 112 forms the luminal surface which surrounds the lumen 122 of the articulating stent-graft 100. The plurality of stent members 116, and unsupported intervening regions 102 form the intermediate region between the first and second tubular shaped biocompatible grafts 112, 114, and the outermost abluminal layer is formed by the second tubular shaped biocompatible graft 114.

Figure 7C:
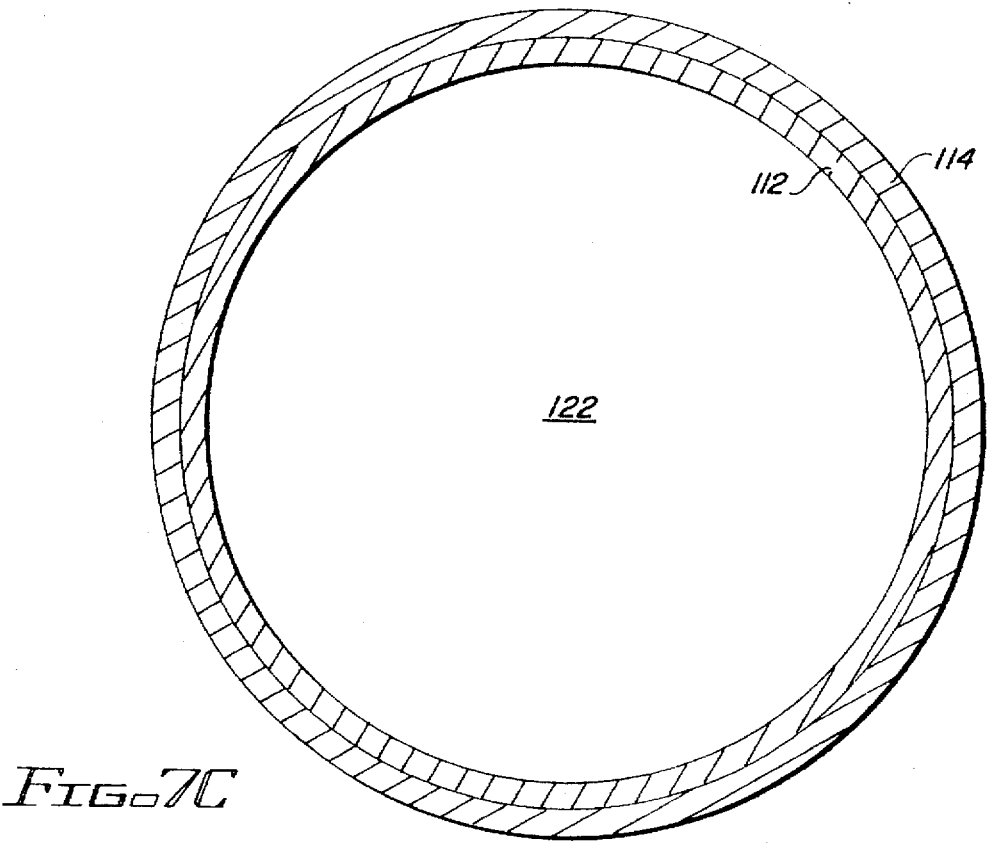
FIG. 7C is a cross-sectional view of the articulated stented graft shown in FIG. 7 taken along line 7C—7C of FIG. 7.

FIG. 7C illustrates the unsupported intervening region 102 of the articulating stent graft. FIG. 7C is a transverse cross-sectional view taken along line 7C—7C of FIG. 7. The first tubular biocompatible graft 112 forms the luminal surface, while the second tubular biocompatible graft 114 forms the abluminal surface of the unsupported intervening region 102 of the articulating stent graft 100.

As with the previously described embodiments of the present invention, the articulating stent graft 100 is assembled using a madrel to mount the first graft member 112, concentrically mount the plurality of stent members 116 circumferentially around the first graft member 112 leaving spaces between adjacent stent members 116 to form the unsupported regions 102, and circumferentially cover the plurality of stent members 116 and the first graft member 112. Both the first and second biocompatible tubular graft members 112, 114 are preferably made of unsintered or partially sintered ePTFE tubular extrudates, are mechanically bonded to one another circumferentially about and longitudinally along the entire stent-graft 100 and through a plurality of openings in each of the plurality of stent members 116, and the entire assembly is heated to the sintering temperature of ePTFE to sinter the first and second biocompatible tubular graft members 112, 114 into a substantially monolithic covering encapsulating the plurality of stent members 116.

Figure 8:
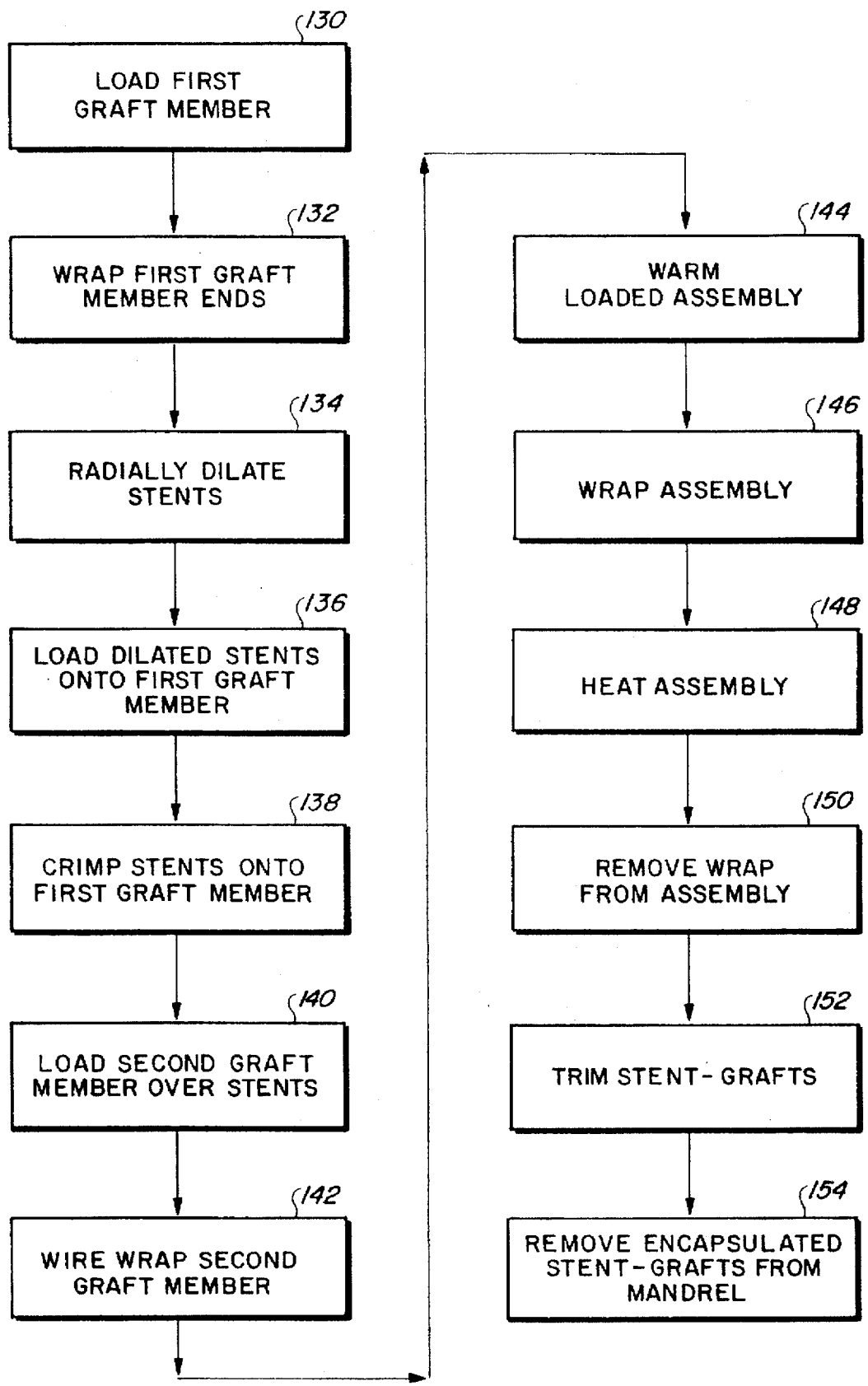
FIG. 8 is a flowchart of the process for making the first preferred embodiment of the encapsulated stent of the present invention.

FIG. 8 illustrates a flow chart which depicts the process for making the preferred embodiment of the radially expanded encapsulated stent. The first step one 130 involves loading a first ePTFE graft onto a mandrel. A section of the first ePTFE graft is then wrapped with wire or tape to prevent migration of the first ePTFE graft on the mandrel in step two 132. The next step, step two 134, comprises pre-dilating one or more stents on a second mandrel. Once the stents are pre-dilated, the stents are loaded over the first ePTFE graft and mandrel and spaced apart evenly along the length of the first ePTFE graft in step four 136. In step five 138, the pre-dilated stents are crimped onto the first graft and mandrel. Subsequent to crimping the pre-dilated stents, a second ePTFE graft is loaded over the crimped stents in step six 140. The next step, step seven 142, requires wrapping the second ePTFE graft at its ends and between the crimped stents with a wire wrap. Next, the assembly comprising the mandrel, the first ePTFE graft, the crimped stents, and the second ePTFE graft is warmed in an oven in step eight 144 to facilitate softening of the ePTFE and increase contact area between the ePTFE layers through the stent. It has been found that step eight 144 is an optional step and is not required to obtain acceptable stent-graft characteristics. After warming, the entire assembly is helically wrapped with TEFLON tape as indicated in step nine 146. In step ten 148, the wrapped assembly is then heated to sintering temperatures. After heating at the sintering temperature of ePTFE, the assembly is removed from the oven, allowed to cool and the tape and wire wraps are removed from the assembly in step eleven 150. Step twelve 152 involves trimming the ePTFE grafts adjacent the ends of the stents to form individual encapsulated stents. Finally, in step thirteen 154, the resulting encapsulated stents are removed from the mandrel.

The following examples describe the preparation of the preferred embodiment of the invention which comprises the tubular shaped encapsulated stent. The examples are meant to be purely illustrative and non-limiting.

EXAMPLE ONE

An unsintered three millimeter (mm) internal diameter (ID) ePTFE vascular graft having a wall thickness of 0.5 mm was loaded onto a 3.56 mm loading mandrel. Opposing ends of the ePTFE vascular graft were wrapped with TEFLON tape to prevent slippage on the mandrel. Two PALMAZ P-128 stents (Johnson & Johnson Interventional Systems, Inc., Warren, N.J.) having an outside diameter of 2.5 mm in its unexpanded condition and an expanded diameter of 12 mm, were pre-dilated on a 5.46 mm tapered mandrel. The pre-dilated stents were then loaded over the 3 mm ePTFE graft and spaced equidistantly at 2 mm intervals from one another along the length of the 3 mm ePTFE graft. Circumferential pressure was applied to the stents to embed them into the outer surface underlying ePTFE graft. Next, an unsintered 4.3 mm ID ePTFE graft having a wall thickness of 0.4 mm was concentrically loaded over the stents and the ePTFE previously mounted on the loading mandrel. The opposing ends of the outer ePTFE graft was wrapped with TEFLON tape, without twisting the ePTFE grafts, to prevent slippage and the opposing ends of the inner and outer ePTFE grafts were wire wrapped onto the assembly. The entire assembly was then tightly wrapped with a helical wrap of TEFLON tape and placed into an sintering oven at 327° C. for ten minutes. The TEFLON taped assembly was then removed from the oven and the TEFLON tape and wire wraps were removed with a continuous tangential pressure to avoid wrinkling the ePTFE. The ePTFE grafts were then cut about one inch from each wrapped end, and the stent-grafts were gently removed from the loading mandrel and cut to provide a 3 mm ePTFE overhang at both ends of the individual stents.

EXAMPLE TWO

A 3 mm ID thin wall ePTFE graft was loaded onto a 3.56 mm mandrel. The top section of the 3 mm ePTFE graft was wrapped with TEFLON tape to prevent migration. Next, three P-394 PALMAZ stents and three P-308 PALMAZ stents were pre-dilated on a 4.74 mm mandrel. The three P-394 pre-dilated stents were loaded first onto the 3 mm ePTFE graft, followed by the three P-308 pre-dilated stents, and then spaced equidistantly from another along the length of the 3 mm ePTFE graft. The pre-dilated stents were then crimped onto the mandrel and a 4 mm ID ePTFE graft was loaded over the crimped stents. The 4 mm ePTFE graft was wire wrapped at both its ends and between the crimped stents. The entire assembly was then placed in an oven for 30 seconds and heated at 340° C. and then removed. The assembly was then wrapped tightly with TEFLON tape with the three P-308 stents being wrapped first. The entire TEFLON tape wrapped assembly was then heated at a sintering temperature of 375° C. for four minutes, reversed, and then heated at 375° C. for another four minutes in order to sinter the ePTFE grafts. The entire assembly was then removed and the TEFLON tape and wires were removed from the assembly. The grafts were then cut approximately one inch from the ends of each of the stents and the resulting encapsulated stents were gently removed from the mandrel one at a time. The ePTFE grafts were then cut to provide a 3 mm overhang at each end of the encapsulated stents.

EXAMPLE THREE

An unsintered three millimeter (mm) internal diameter (ID) ePTFE vascular graft having a wall thickness of 0.5 mm was loaded onto a 3.56 mm loading mandrel. Opposing ends of the ePTFE vascular graft were with secured with TEFLON tape to prevent slippage on the mandrel. Six PALMAZ P-128 stents, each having an outside diameter of 2.5 mm in their unexpanded condition and a maximum expanded diameter of 12 mm, were pre-dilated on a 5.46 mm tapered mandrel. After removal from the tapered mandrel, the stents recoiled to a pre-dilated outside diameter of 5.29 mm. The pre-dilated stents were then loaded over the 3 mm ePTFE graft and spaced equidistantly at 2 mm intervals from one another along the length of the 3 mm ePTFE graft.

Circumferential pressure was applied to the stents to embed them into the outer surface underlying ePTFE graft. Next, an unsintered 4.3 mm ID ePTFE graft having a wall thickness of 0.4 mm was concentrically loaded over the stents and the ePTFE previously mounted on the loading mandrel. The opposing ends of the outer ePTFE graft was wrapped with TEFLON tape, without twisting the ePTFE grafts, to prevent slippage and the opposing ends of the inner and outer ePTFE grafts were wire wrapped onto the assembly. The entire assembly was then tightly wrapped with a helical wrap of TEFLON tape applied at 1.8 psi on a DC powered helical wrapping machine, and placed into an sintering oven at 327° C. for ten minutes. The TEFLON taped assembly was then removed from the oven and the TEFLON tape and wire wraps were removed with a continuous tangential pressure to avoid wrinkling the ePTFE. The ePTFE grafts were then cut about one inch from each wrapped end, and the stent-graft assembly was gently removed as a unit from the loading mandrel and cut to provide a 3 mm ePTFE overhang at both ends of the stent-graft assembly.

The above-described examples formed encapsulated stents which appeared to comprise monolithic structures incapable of complete separation or delamination from the stent under conditions of endoluminal delivery, radial expansion and stent-graft patency within the body. Prior experiments produced structures having inner ePTFE graft layers which pulled away from the stent wall upon removal from the mandrel. This non-bonding problem was solved, as evidenced in the above-described examples, by using unsintered freshly expanded ePTFE extrudate to increase bond strength between the luminal and abluminal ePTFE grafts.

The ePTFE grafts preferably comprise initial internodal distances (INDs) within a range of 0.1 to 100 microns. Further, the inner and outer ePTFE grafts which comprise the radially expandable encapsulated stent may have different INDs and wall thicknesses to facilitate radial expansion and promote healing and tissue ingrowth.

All tubular embodiments of the radially expandable reinforced vascular graft are designed to be used with conventional balloon catheters making the delivery system for the device simple, easily accessible, and cost effective. Once the stent graft positioned endoluminally, the stent graft is radially expanded using an angioplasty balloon. During expansion, the ePTFE encapsulation radially expands, with a concomitant change in the node-fibril microstructure due to radial expansion of the ePTFE, as depicted in FIGS. 18–20 illustrating the abluminal wall surface, the luminal wall surface and a cross-section through the ePTFE encapsulation for the unexpanded stent-graft and the unexpanded stent-graft. While some separation occurs between the luminal and abluminal layers of the ePTFE encapsulation, which is believed due to tearing of the bonded layers by movement of the stent struts through the ePTFE material, it has been found that at least 30% of the monolithic ePTFE encapsulation remains fully and integrally bonded. After radial expansion, the encapsulated stent-graft has the visual appearance of an ePTFE tubular graft with a stent imbedded between luminal and abluminal ePTFE walls.

FIGS. 9–20 are photomicrographs and electron micrographs of the inventive stent-graft assembly.

Figure 9:
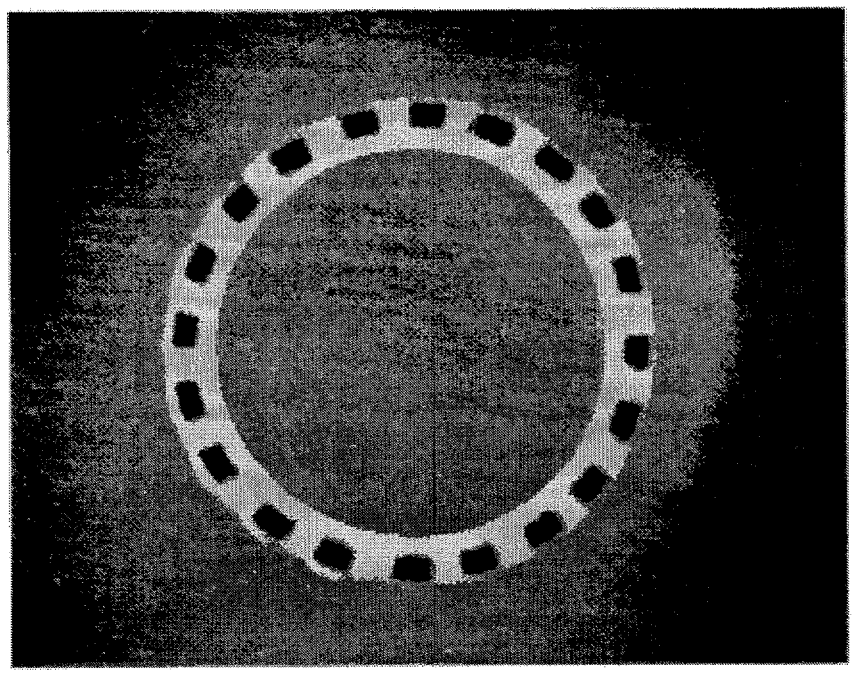
FIG. 9 is a photomicrograph taken under a light microscope at 12× magnification of a transverse cross-sectional view of the inventive stent-graft assembly in its radially unexpanded condition.

FIG. 9 is a photomicrograph transverse cross-sectional view of the sintered unexpanded stent-graft assembly showing the stent struts embedded and encased within the luminal and abluminal ePTFE grafts. The ePTFE encapsulation appears to be continuous and without interlayer demarcation.

Figure 10:
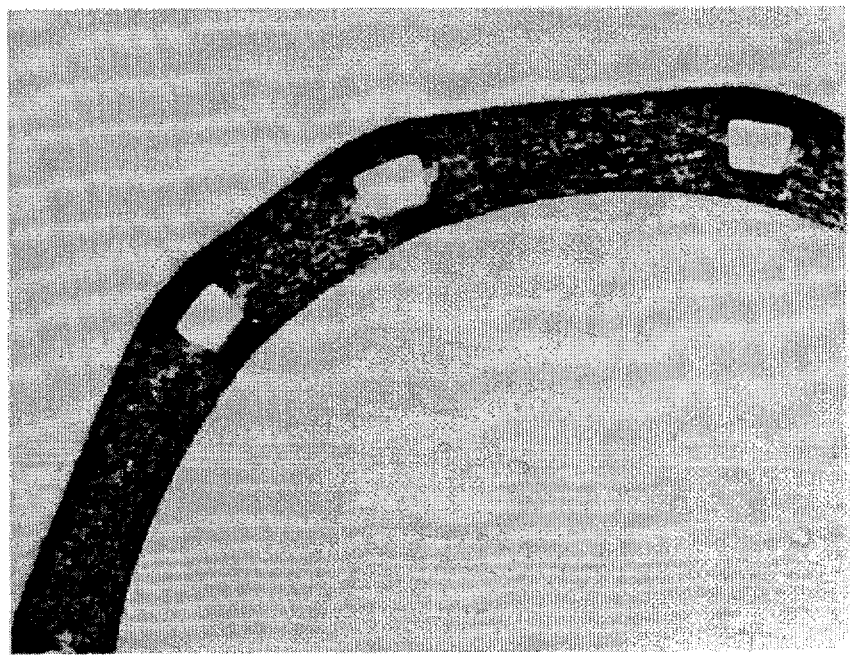
FIG. 10 is a photomicrograph taken by scanning electron microscopy of a partial transverse cross-sectional view of a radially unexpanded encapsulated stent-graft assembly in accordance with the present invention.

FIG. 10 is a higher magnification photomicrograph of an arcuate transverse cross-section of the stent-graft assembly depicted in FIG. 9. Again the stent struts appear embedded and encased within the luminal and abluminal ePTFE grafts and the ePTFE encapsulation appears to be continuous and without interlayer demarcation.

Figure 11:
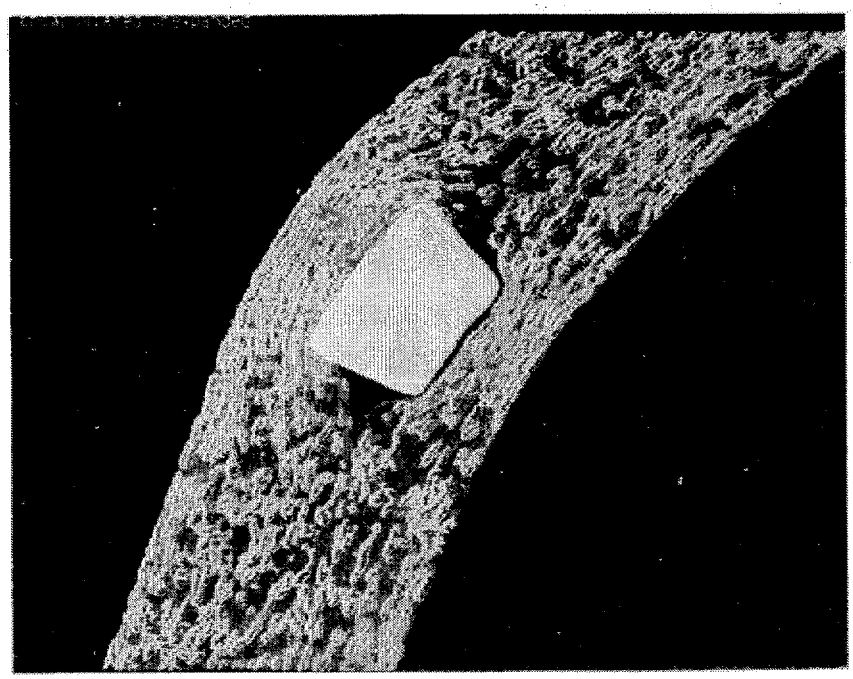
FIG. 11 is a scanning electron micrograph of a partial transverse cross-sectional view illustrating a section of a radially unexpanded encapsulated stent-graft assembly taken at 100× magnification.

FIG. 11 is an electron micrograph of a transverse cross-section of an unexpanded inventive stent-graft assembly showing a single stent strut encapsulated between the luminal and abluminal ePTFE grafts. It will be noted that the ePTFE appears to be completely and integrally bonded as a monolithic structure surrounding the stent strut, without interlayer demarcation and without significant void space adjacent the stent strut.

Figure 12:
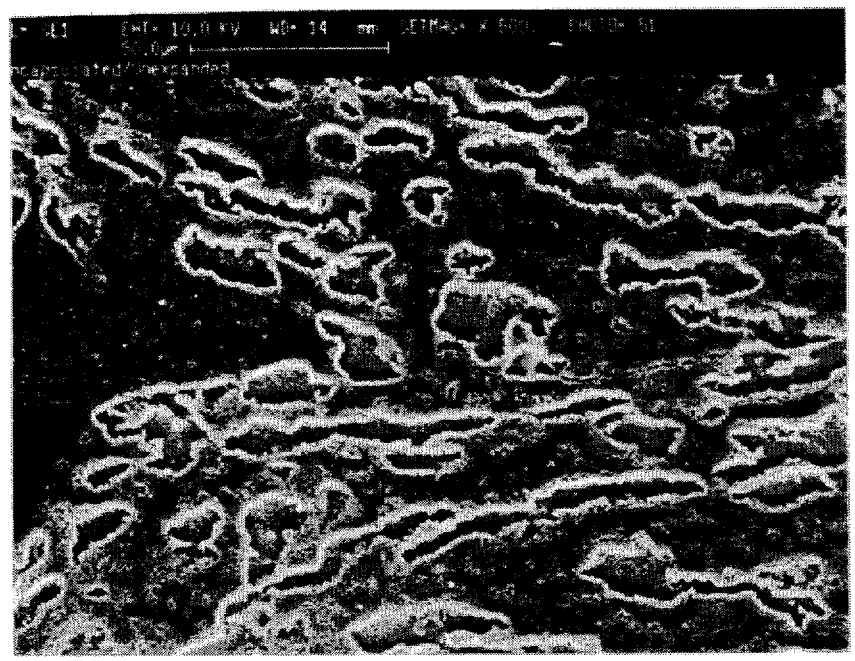
FIG. 12 is a scanning electron micrograph of a partial transverse cross-sectional view taken at 500× magnification of a section of the radially unexpanded encapsulated stent-graft assembly of FIG. 11.

FIG. 12 is a higher magnification electron micrograph of the same section as illustrated in FIG. 11, taken adjacent the stent strut showing the small void space where the luminal and abluminal ePTFE grafts bond. It will be understood, by those skilled in the art, the luminal and abluminal ePTFE grafts appear fully bonded as an integral monolithic structure without any substantial demarcation between the bonded layers.

Figure 13:
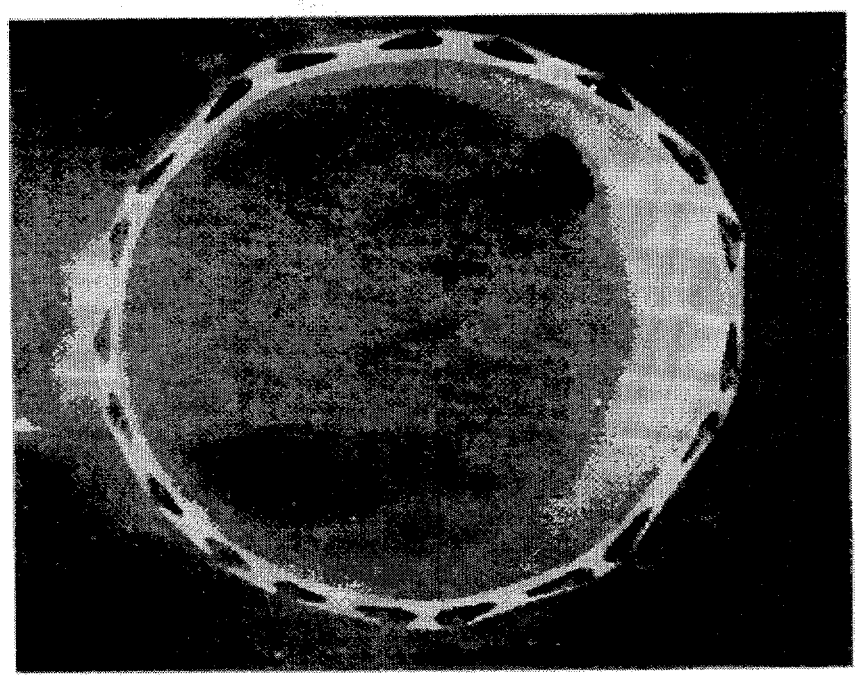
FIG. 13 is a photomicrograph taken by light microscopy taken at 5.5× magnification of a transverse cross-section of a radially expanded stent-graft assembly in accordance with the present invention.

FIG. 13 is a photomicrograph of a transverse cross-section of a radially expanded stent-graft assembly. When compared to FIG. 9, it will be understood that the stent struts have been displaced during radial expansion, creating the void spaces adjacent the stent struts. However, it will also be noted that substantial bonded areas of the ePTFE luminal and abluminal grafts remain between adjacent struts.

Figure 14:
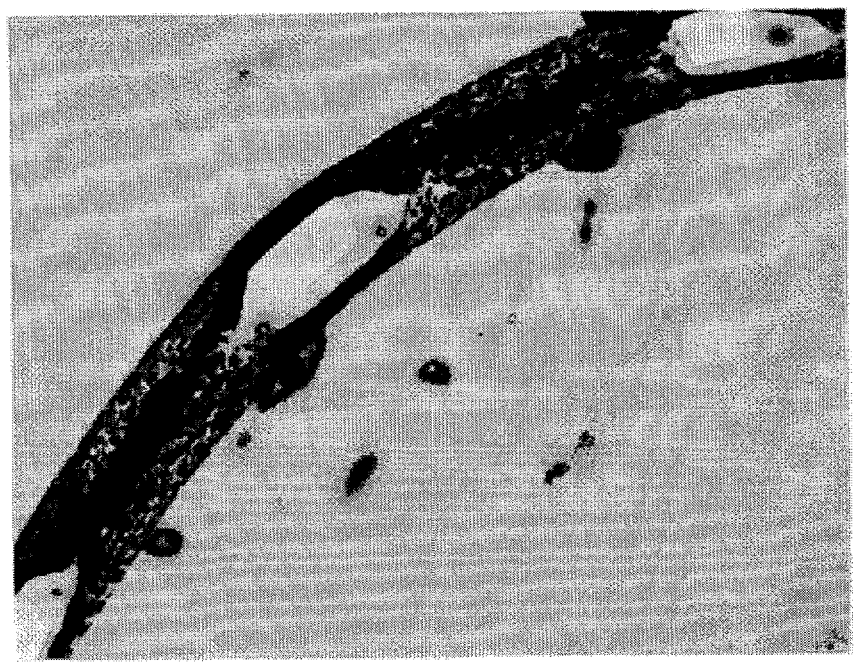
FIG. 14 is a photomicrograph taken by light microscopy at 37.5× magnification showing a partial transverse cross-sectional view of a radially expanded encapsulated stent-graft in accordance with the present invention.

FIG. 14 is a higher magnification photomicrograph taken of a transverse cross-section of an arcuate portion of the radially expanded stent-graft, as depicted in FIG. 13. It will be understood that substantial regions of bonded ePTFE remain between adjacent struts after radial expansion of the stent-graft.

Figure 15:
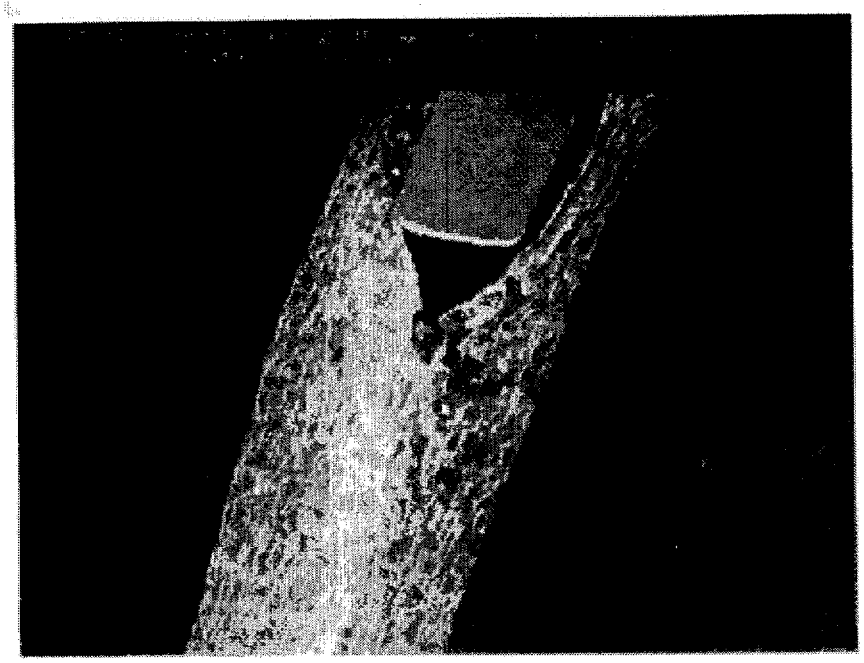
FIG. 15 is a scanning electron micrograph at 100× magnification of a transverse cross-sectional portion of a radially expanded encapsulated stent-graft in accordance with the present invention.
Figure 16:
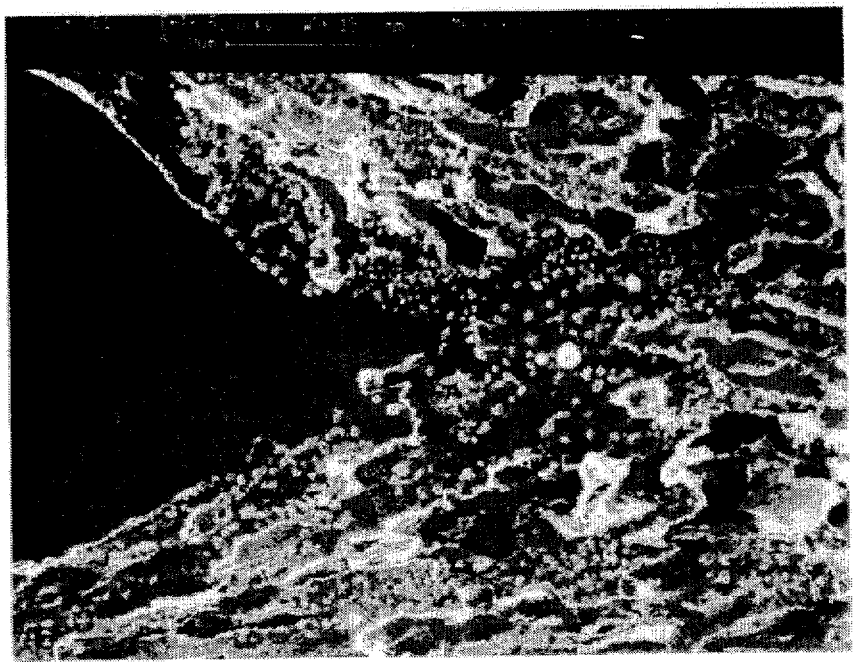
FIG. 16 is a scanning electron micrograph taken at 500× magnification of a section of the radially expanded encapsulated stent-graft in FIG. 15.
Figure 17:
FIG. 17 is a scanning electron micrograph of a transverse cross-sectional view of a stent strut and encapsulating first and second ePTFE layers of a freeze-fractured radially expanded encapsulated stent graft.

FIGS. 15–17 are electron micrographs illustrating lower and higher magnification views of the same transverse cross-sectional area of a radially expanded stent-graft. When compared to FIG. 11, it will be seen in FIG. 15 that a void space has been created adjacent the stent strut due to radial expansion of the stent graft. In FIG. 16, however, it will be seen that the void space created during radial expansion of the stent-graft is confined and does not propagate into the adjacent ePTFE bonded area, which is noticeably free of fracture lines. FIG. 17 is a scanning electron micrograph illustrating the void area as in FIG. 16, again illustrating that the void area created during radial expansion of the stent-graft is confined and does not propagate into the adjacent ePTFE bonded area.

Figure 18A:
FIG. 18A is a scanning electron micrograph taken at 200× magnification of an abluminal wall surface of the inventive stent-graft in its radially unexpanded diameter.
Figure 18B:
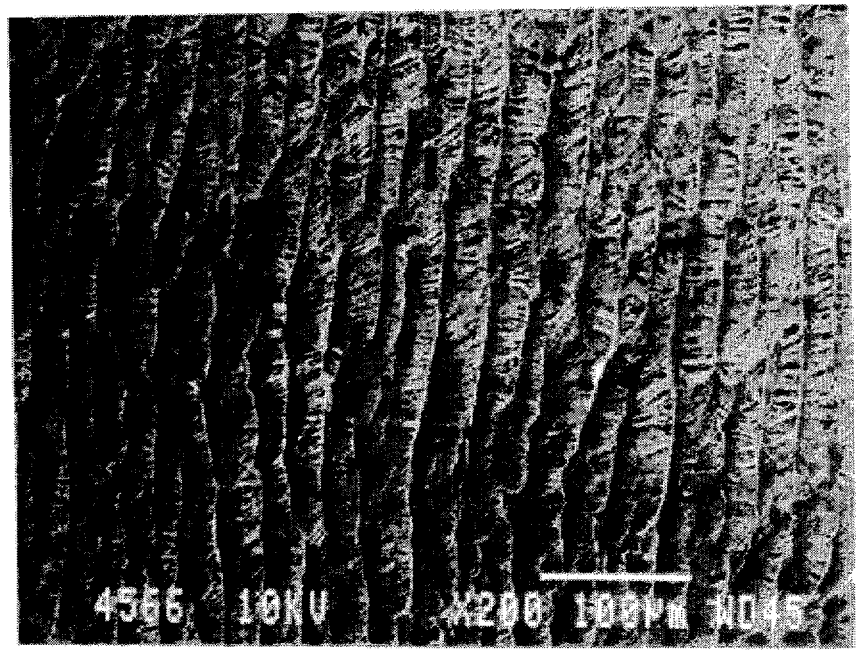
FIG. 18B is a scanning electron micrograph taken at 200× magnification of an abluminal wall surface of the inventive stent-graft in its radially expanded diameter.
Figure 19A:
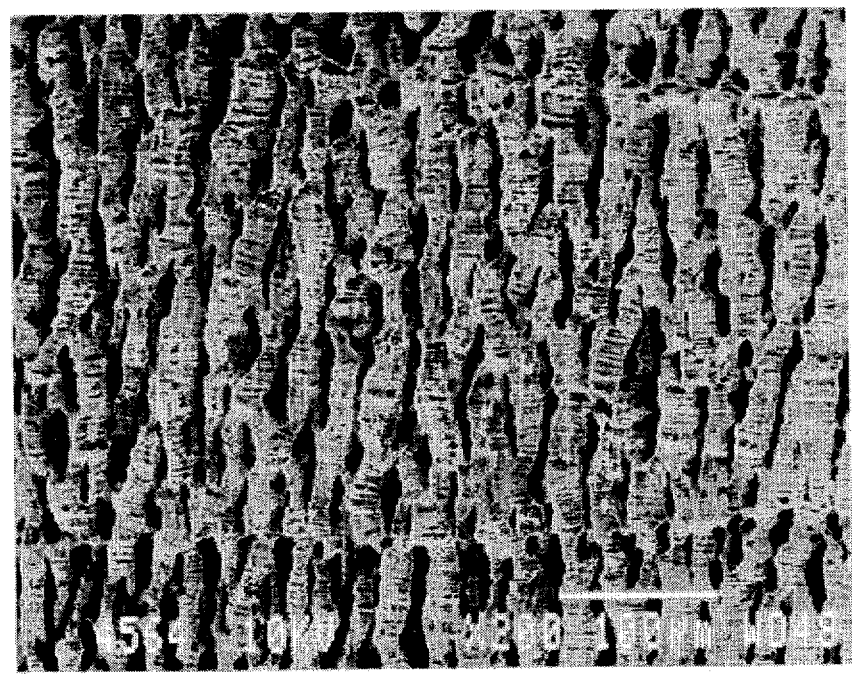
FIG. 19A is a scanning electron micrograph taken at 200× magnification of a luminal wall surface of the inventive stent-graft in its radially unexpanded diameter and showing a stent strut underlying the ePTFE covering.
Figure 19B:
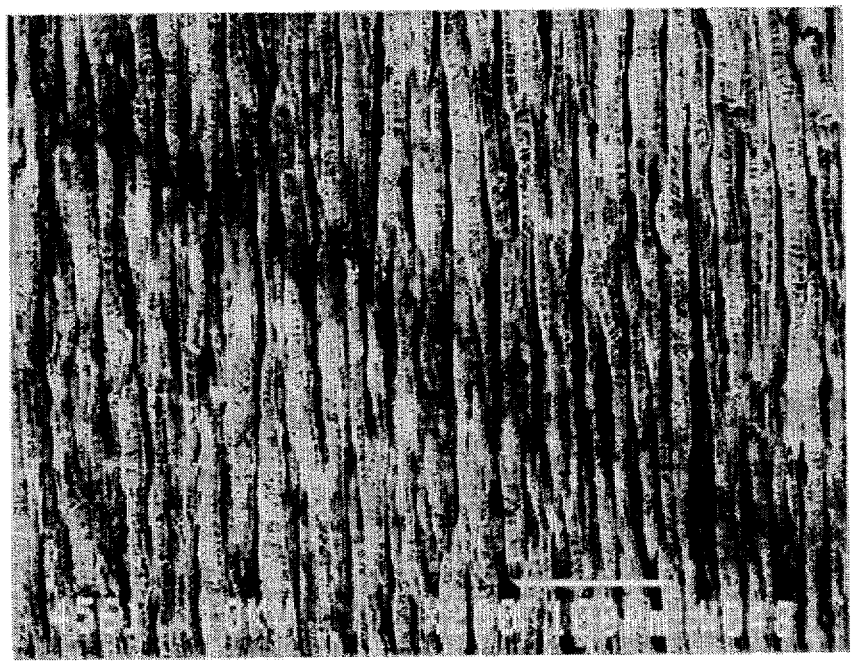
FIG. 19B is a scanning electron micrograph taken at 200× magnification of a luminal wall surface of the inventive stent-graft in its radially expanded diameter and showing a stent strut underlying the ePTFE covering.
Figure 20A:
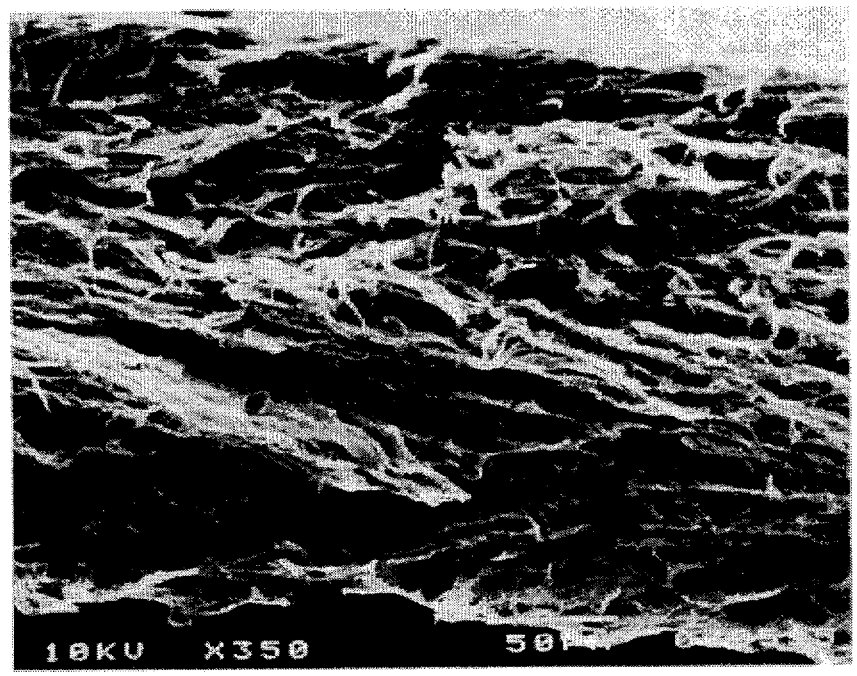
FIG. 20A is a scanning electron micrograph taken at 350× magnification of a partial transverse cross-sectional view of freeze fractured radially unexpanded bonded luminal and abluminal ePTFE grafts.
Figure 20B:
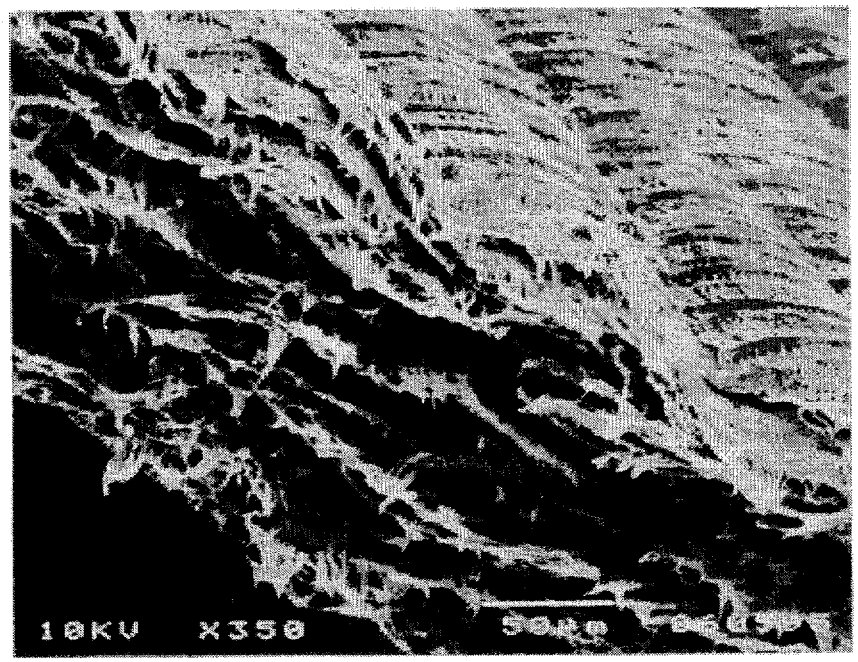
FIG. 20B is a scanning electron micrograph taken at 350× magnification of a partial transverse cross-sectional view of freeze fractured radially expanded bonded luminal and abluminal ePTFE grafts.

FIGS. 18A and 18B are electron micrographs taken of the outer luminal wall surface of the inventive stent-graft assembly, in its unexpanded and expanded state, respectively. FIGS. 19A and 19B are electron micrographs taken of the inner luminal wall, showing underlying stent struts, in its unexpanded and expanded state, respectively. Finally, FIGS. 20A and 20B are scanning electron micrographs of freeze fractured cross-sections of luminal and abluminal grafts sintered together without in intervening stent using the method of the present invention, in a radially unexpanded and radially expanded conditions, respectively. From each of FIGS. 18A–20B, it can readily be seen that when the stent-graft is radially expanded, the ePTFE node-fibril microstructure undergoes nodal elongation in the axis of radial expansion while the bonded area of sintered ePTFE in the wall thickness remains integrally and monolithically bonded, and substantially without interlayer demarcation.

As illustrated in these micrographs, PTFE extrudate which is longitudinally expanded has a characteristic node and fibril microstructure in which the fibrils are uniaxially oriented parallel to the axis of longitudinal expansion. When a sintered tubular ePTFE graft is radially expanded, fibril length remains substantially constant, but there is a elongation of the nodes along the axis of radial expansion and substantially perpendicular to the axis of longitudinal expansion of the ePTFE tubular graft. Upon radial expansion of any of the embodiments of the encapsulated stent-graft of the present invention, nodal elongation is found. Thus, with the present invention, radial expansion of the stent occurs with a concomitant change in the node-fibril microstructure of the ePTFE encapsulation surrounding the stent.

Finally, as illustrated in FIG. 21, a sheath-less stent-graft delivery system 150 is illustrated. When mounted onto a balloon catheter 152 for percutaneous delivery, the inventive stent-graft 160 mounted concentrically over the dilatation balloon 154 and proximal to an atraumatic catheter tip, provides a sheath-less delivery system. Because the encapsulated stent-graft 160 has an abluminal covering of ePTFE encapsulated around the underlying stent, the encapsulated stent-graft 160 protects the underlying balloon 154, protects the anatomical passageway from trauma due to the stent, and provides a low friction external surface to facilitate intraluminal delivery.

While the invention has been described with reference to preferred embodiments thereof the description is for illustrative purposes only and is not to be construed as limiting the scope of the invention. Various modifications and changes may be made by those skilled in the art without departing from the true spirit of the scope of the invention as defined by the appended claims.

We claim:

1. A radially expandable reinforced vascular graft comprising:
   at least one tubular radially expandable support member having a plurality of openings passing through walls of the support member, and
   an expanded polytetrafluoroethylene tubular member circumferentially surrounding and at least substantially enclosing the at least one tubular radially expandable support member and passing into and through the plurality of openings passing through the walls of the support member, the expanded polytetrafluoroethylene tubular member being radially expandable with the support member to an expanded diameter; wherein the expanded polytetrafluoroethylene tubular member further comprises a node-fibril microstructure which undergoes nodal elongation during radial expansion to the expanded diameter.

2. The radially expandable reinforced vascular graft of claim 1 wherein the expanded polytetrafluoroethylene tubular member further comprises first and second expanded polytetrafluoroethylene graft members joined together thereby forming an integral structure passing through the openings of said support layer and substantially covering said support.

3. The radially expandable reinforced vascular graft of claim 1 wherein the plurality of openings in the support member are separated by a plurality of struts and the expanded polytetrafluoroethylene tubular member passes through said plurality of openings and between the plurality of struts.

4. The radially expandable reinforced vascular graft of claim 1 wherein the support member further comprises at least one of silver, titanium, Nitinol, stainless steel, gold alloy, tantalum and any suitable plastic material which is radially expandable and resists radial collapse.

5. The radially expandable reinforced vascular graft of claim 1 wherein the support member comprises a stent.

6. The radially expandable reinforced vascular graft of claim 5 wherein the expanded polytetrafluoroethylene tubular member is characterized by having internodal distances within the range of 0.10 to 100 microns.

7. The radially expandable reinforced vascular graft of claim 5 wherein the stent further comprises a balloon expandable stent.

8. The radially expandable reinforced vascular graft of claim 5, wherein the stent further comprises a self-expanding stent.

9. The radially expandable reinforced vascular graft of claim 5, wherein the stent further comprises a nitinol stent.

10. The radially expandable reinforced vascular graft of claim 1, wherein the expanded polytetrafluoroethylene tubular member further comprises first and second expanded polytetrafluoroethylene graft members, the first expanded polytetrafluoroethylene graft member positioned concentrically about an abluminal surface of the at least one radially expandable tubular support member and the second expanded polytetrafluoroethylene graft member positioned concentrically within and adjacent to a luminal surface of the at least one radially expandable tubular support member.

11. The radially expandable reinforced vascular graft of claim 10, wherein the first expanded polytetrafluoroethylene graft member and the second expanded polytetrafluoroethylene graft member have internodal distances which are different from one another.

12. The radially expandable reinforced vascular graft of claim 10, wherein wall thicknesses of said first expanded polytetrafluoroethylene graft member and said second expanded polytetrafluoroethylene graft member are different from one another.

13. The radially expandable reinforced vascular graft of claim 10, wherein the first and second expanded polytetrafluoroethylene tubular members are monolithically bonded to one another together through the openings passing through the at least one radially expandable tubular support member.

14. A radially expandable reinforced vascular graft comprising:
   at least one radially expandable tubular support member having a plurality of openings passing through walls thereof; and
   at least one longitudinally expanded polytetrafluoroethylene tubular member circumferentially surrounding the at least one radially expandable tubular support member on luminal and abluminal surfaces thereof such that the at least one radially expandable tubular support member is interdisposed and circumferentially enclosed over at least a substantial longitudinal extent thereof; the at least one longitudinally expanded polytetrafluoroethylene tubular member passing through the plurality of openings in the walls of the tubular support member and radially expandable substantially concurrently with the tubular support member to an expanded diameter; wherein the at least one longitudinally expanded polytetrafluoroethylene tubular member further comprises a node-fibril microstructure which undergoes nodal elongation during radial expansion to the expanded diameter.

15. The radially expandable reinforced vascular graft of claim 14, wherein the at least one radially expandable tubular support member further comprises a tubular stent having a plurality of openings separated by a plurality of struts.

16. The radially expandable vascular graft according to claim 14, wherein the at least one longitudinally expanded polytetrafluoroethylene tubular member further comprises a biased laminate of first and second longitudinally expanded polytetrafluoroethylene tubular members concentrically joined to one another.

17. The radially expandable reinforced vascular graft of claim 14 wherein the first and second longitudinally expanded polytetrafluoroethylene tubular members are monolithically joined to one another and surround first and second ends of said radially expandable tubular support member.

18. The radially expandable reinforced vascular graft of claim 14, wherein said first and second longitudinally expanded polytetrafluoroethylene tubular members further have internodal distances within the range of 0.10 to 100 microns.

19. The radially expandable reinforced vascular graft of claim 18, wherein the first and second longitudinally expanded polytetrafluoroethylene tubular members are selected to have at least one of differing internodal distances and wall thickness.

20. The radially expandable reinforced vascular graft of claim 14, wherein the at least one radially expandable tubular support member comprises at least two radially expandable tubular shaped support members positioned at predetermined distances from one another such that said radially expandable tubular shaped support members are positioned at opposing ends of each of the at least two longitudinally expanded polytetrafluoroethylene tubular members with an intermediate longitudinal region of the at least two radially expanded polytetrafluoroethylene tubular members being unsupported by a radially expandable tubular shaped support member.

21. The radially expandable vascular graft according to claim 14, wherein the at least one radially expandable tubular support member further comprises an endoluminal stent selected from the group consisting of balloon expandable stents, self expanding stents and nitinol stents.

* * * * *